United States Patent
Hu et al.

(10) Patent No.: US 11,191,493 B2
(45) Date of Patent: *Dec. 7, 2021

(54) METHOD AND APPARATUS FOR PREDICTING A NEED FOR A BLOOD TRANSFUSION

(71) Applicant: The University of Maryland, Baltimore, Baltimore, MD (US)

(72) Inventors: Fu-Ming Hu, Ellicott City, MD (US); Colin Mackenzie, Pasadena, MD (US); Shiming Yang, Halethrope, MD (US); Hegang Chen, Ellicott City, MD (US)

(73) Assignee: The University of Maryland, Baltimore, Baltimore, MD (US)

( * ) Notice: Subject to any disclaimer, the term of this patent is extended or adjusted under 35 U.S.C. 154(b) by 304 days.

This patent is subject to a terminal disclaimer.

(21) Appl. No.: 16/288,207

(22) Filed: Feb. 28, 2019

(65) Prior Publication Data

US 2019/0328338 A1    Oct. 31, 2019

Related U.S. Application Data

(63) Continuation of application No. 14/911,421, filed as application No. PCT/US2014/050790 on Aug. 12, 2014, now Pat. No. 10,258,292.

(51) Int. Cl.
*A61B 5/00* (2006.01)
*A61B 5/1455* (2006.01)
(Continued)

(52) U.S. Cl.
CPC .......... *A61B 5/7275* (2013.01); *A61B 5/0205* (2013.01); *A61B 5/02042* (2013.01);
(Continued)

(58) Field of Classification Search
CPC . A61B 5/0205; A61B 5/1455; A61B 5/14551; A61B 5/14552; A61B 5/0059;
(Continued)

(56) References Cited

U.S. PATENT DOCUMENTS 7,035,679 B2    4/2006  Addison et al.
8,512,260 B2    8/2013  Grudic et al.
(Continued)

FOREIGN PATENT DOCUMENTS

WO    2013/070864 A2    5/2013
WO    2015/023708 A1    2/2015

OTHER PUBLICATIONS

International Search Report and Written Opinion, International Patent Application No. PCT/US14/050790, dated Jan. 12, 2015, pp. 1-10.

(Continued)

*Primary Examiner* — Chu Chuan Liu
(74) *Attorney, Agent, or Firm* — Wolter Van Dyke Davis, PLLC; Eugene J. Molinelli; Cian O'Brien

(57) ABSTRACT

A method is provided for predicting that a patient will require a blood transfusion during a treatment. The method includes obtaining, on a processor, first data that indicates values for one or more parameters of a characteristic of a continuous photoplethysmographic (PPG) waveform collected during the treatment. The method further includes applying, on the processor, coefficients to the values for the one or more parameters. The method further includes determining, on the processor, second data that indicates a prediction that the patient will require the blood transfusion during the treatment based on applying the coefficients to the values for the one or more parameters. An apparatus is also provided for predicting that the patient will require the blood transfusion during the treatment.

20 Claims, 7 Drawing Sheets

(51) Int. Cl.
    *G16H 50/20* (2018.01)
    *A61B 5/0205* (2006.01)
    *A61B 5/024* (2006.01)
    *A61B 5/02* (2006.01)
    *G16H 20/40* (2018.01)

(52) U.S. Cl.
    CPC ........ *A61B 5/02416* (2013.01); *A61B 5/4836* (2013.01); *A61B 5/742* (2013.01); *G16H 20/40* (2018.01); *G16H 50/20* (2018.01); *A61B 5/14551* (2013.01)

(58) Field of Classification Search
    CPC ... A61B 5/7275; A61B 5/02416; A61B 5/742; A61B 5/4836; A61B 5/02042
    See application file for complete search history.

(56) References Cited

U.S. PATENT DOCUMENTS

| | | |
|---|---|---|
| 2008/0082366 A1 | 4/2008 | Miller et al. |
| 2010/0081942 A1 | 4/2010 | Huiku |
| 2010/0099964 A1 | 4/2010 | O'Reilly et al. |
| 2011/0040713 A1 | 2/2011 | Colman et al. |
| 2011/0172545 A1 | 7/2011 | Grudic et al. |
| 2011/0201905 A1 | 8/2011 | Spencer |
| 2012/0016685 A1 | 1/2012 | Ryan et al. |
| 2012/0330117 A1 | 12/2012 | Grudic et al. |
| 2013/0172759 A1 | 7/2013 | Melker et al. |
| 2013/0245397 A1 | 9/2013 | Grudic et al. |

OTHER PUBLICATIONS

Moulton, S. L., et al., Running on empty? The compensatory reserve index, J Trauma Acute Care Surg, 2013, pp. 1053-1059, vol. 75.
Galvan, S., Algorithm Gauges When Patients Are in Danger, The Innovator: USAISR Public Affairs, 2013, 1 page.
EPO: Partial Supplementary Search Report, European U.S. Appl. No. 14835769.2, dated Feb. 15, 2017, pp. 1-7.
CIPO: Official Action, Canadian Patent Application No. 2,920,363, dated Nov. 23, 2016, 3 pages.
CIPO: Office Action, Canadian Patent Application No. 2,920,363, dated Sep. 28, 2017, pp. 1-5.
EPO: Search Report, European Patent Application No. 14835769.2, dated Jun. 9, 2018, pp. 1-8.
Mackenzie et al., Automated prediction of early blood transfusion and mortality in trauma patients, J Trauma Acute Dare Surg, 2014, pp. 1379-1385, vol. 76.

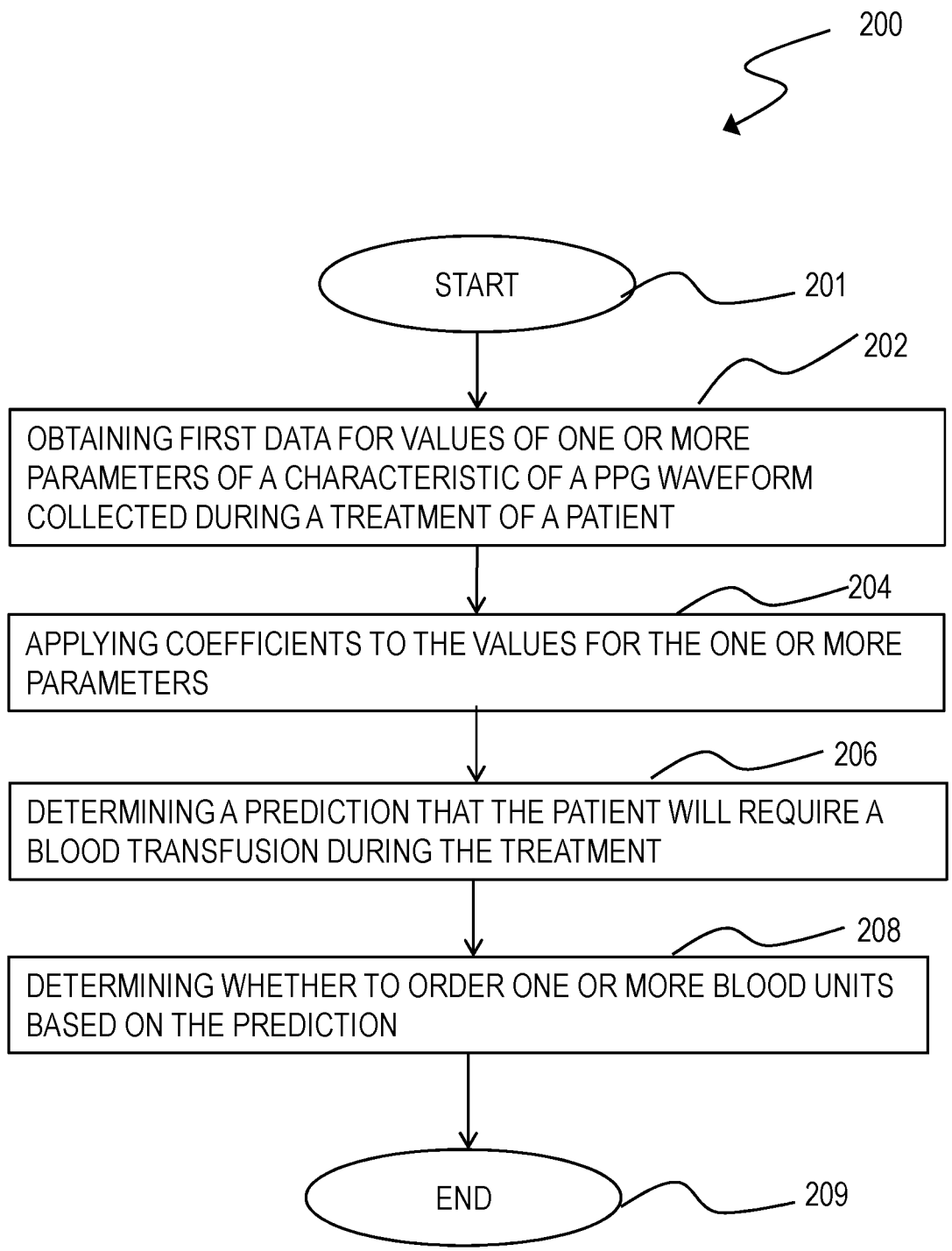

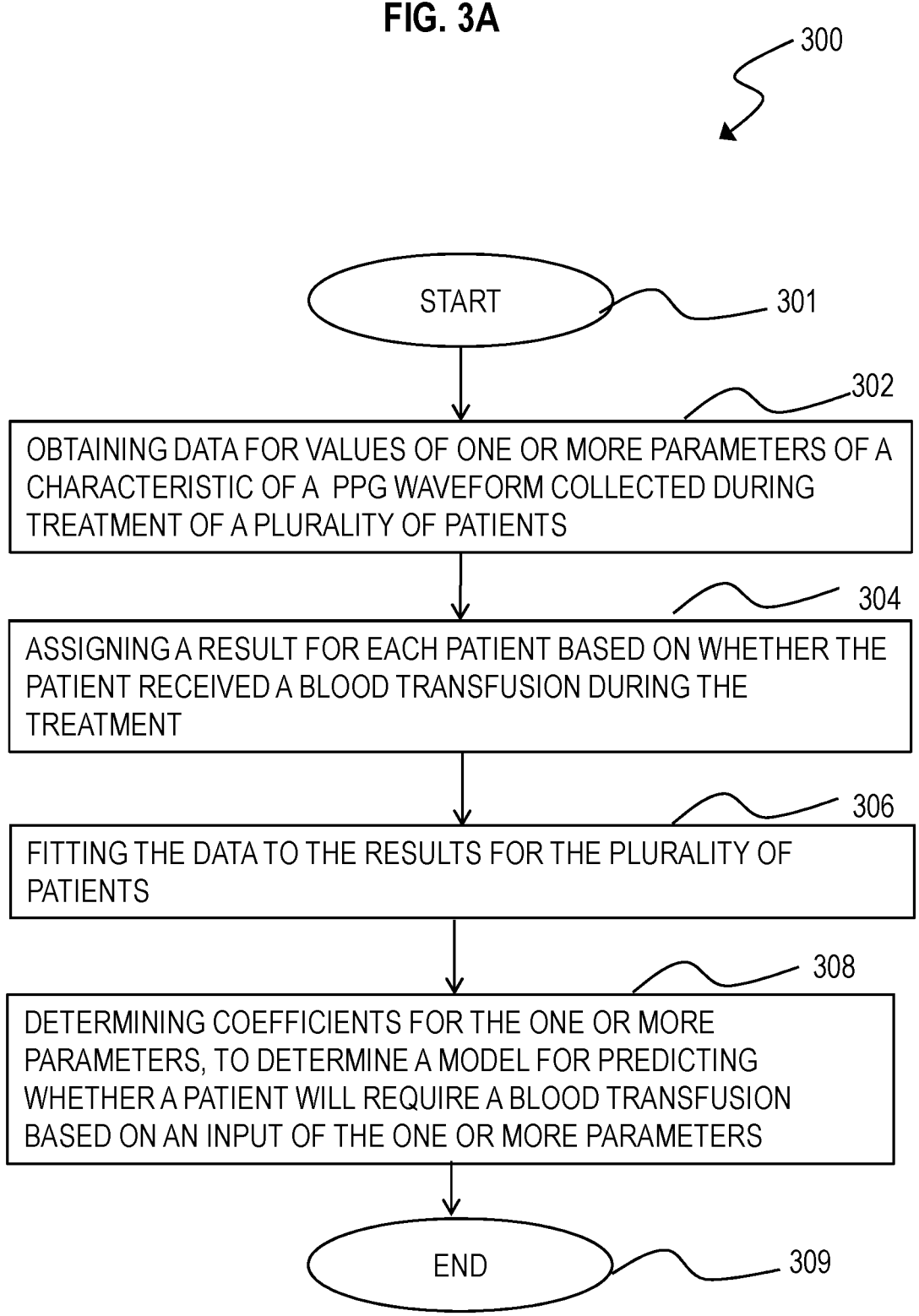

METHOD AND APPARATUS FOR PREDICTING A NEED FOR A BLOOD TRANSFUSION

CROSS-REFERENCE TO RELATED APPLICATIONS

This application is a continuation of U.S. patent application Ser. No. 14/911,421 filed Feb. 10, 2016, which is a 371 National Stage Application of PCT Application No. PCT/US14/50790 filed Aug. 12, 2014, claims benefit of Provisional Application No. 61/864,832 filed Aug. 12, 2013, the entire contents of which are hereby incorporated by reference as it fully set forth herein, under 35 U.S.C. § 119(e).

STATEMENT OF GOVERNMENTAL INTEREST

This invention was made with government support under Contract No. FA8650-11-2-6D01 awarded by the United States Air Force. The government has certain rights in the invention.

BACKGROUND OF THE INVENTION

When a patient suffers a trauma-related injury, they may experience massive blood loss. After admission to a medical facility, the patient may require a blood transfusion. However, a conventional method for determination of whether the patient requires the blood transfusion may not be made until after a substantial amount of time and a substantial amount of blood loss after admission. Thus, it would be desirable to have a method for determining whether the patient requires the blood transfusion at an early stage of the treatment process. Various conventional methods have been proposed, for determining whether the patient requires the blood transfusion during the treatment process.

SUMMARY OF THE INVENTION

The conventional methods for determining whether a patient requires a blood transfusion are deficient in the timing and accuracy of the need for the transfusion. Therefore, a method and apparatus are provided for enhanced prediction of the need for a blood transfusion.

In a first set of embodiments, a method is provided for predicting that a patient will require a blood transfusion during a treatment. The method includes obtaining, on a processor, first data that indicates values for one or more parameters of a characteristic of a continuous photoplethysmographic (PPG) waveform collected during the treatment. The method further includes applying, on the processor, coefficients to the values for the one or more parameters. The method further includes determining, on the processor, second data that indicates a prediction that the patient will require the blood transfusion during the treatment based on applying the coefficients to the values for the one or more parameters.

In some embodiments of the first set, the method further includes determining, on the processor, whether to order one or more blood units based on the prediction. In some embodiments of the first set, the first data is collected over a fixed time interval, the characteristic of the PPG waveform is one or more of a heart rate and an oxygen saturation, and the parameters are one or more of a percentage of the fixed time interval that the heart rate is below a threshold heart rate, a percentage of the fixed time interval that the oxygen saturation is below a threshold saturation rate, a first percentile of the oxygen saturation and a second percentile of the oxygen saturation rate over the fixed time interval, where the second percentile is greater than the first percentile. In some embodiments of the first set, the first data is collected over a fixed time interval and the parameter is a percentile of an amplitude of the PPG waveform collected over the fixed time interval.

In a second set of embodiments, a method is provided for determining a model for predicting whether a patient will require a blood transfusion. The method includes obtaining, on a processor, data that indicates values for one or more parameters of a characteristic of a PPG waveform during treatment of a plurality of patients. The method also includes assigning, on the processor, a result for each patient based on whether the patient received a blood transfusion during the treatment. The method also includes fitting, on the processor, the data to the results for the plurality of patients. The method also includes determining, on the processor, coefficients for the one or more parameters, to determine the model for predicting whether a patient will require a blood transfusion based on an input of the one or more parameters.

In a third set of embodiments, an apparatus is provided for predicting that a patient will require a blood transfusion during a treatment. The apparatus includes a pulse oximeter configured to measure first data that indicates values for one or more parameters of a characteristic of a PPG waveform collected during a treatment of a patient. The apparatus further includes a processor connected to the pulse oximeter and configured to receive the first data of the one or more parameters. The apparatus further includes a memory including a sequence of instructions. The memory and the sequence of instructions are configured to, with the processor, cause the apparatus to apply coefficients to the values for the one or more parameters, and determine second data that indicates a prediction that the patient will require the blood transfusion during the treatment based on applying the coefficients to the values for the one or more parameters.

In a fourth set of embodiments, a computer-readable medium is provided carrying one or more sequences of instructions, where execution of the one or more sequences of instructions by a processor causes the processor to perform the steps of applying coefficients to values for one or more parameters of a characteristic of a PPG waveform collected during a treatment of a patient and determining a prediction that the patient will require a blood transfusion during the treatment based on applying the coefficients to the values for the one or more parameters.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2 is a flow diagram that illustrates an example of a method for predicting that a patient will require a blood transfusion during a treatment, according to one embodiment;

FIG. 3A is a flow diagram that illustrates an example of a method for determining a model for predicting whether a patient will require a blood transfusion, according to one embodiment;

DETAILED DESCRIPTION

Figure 1A:
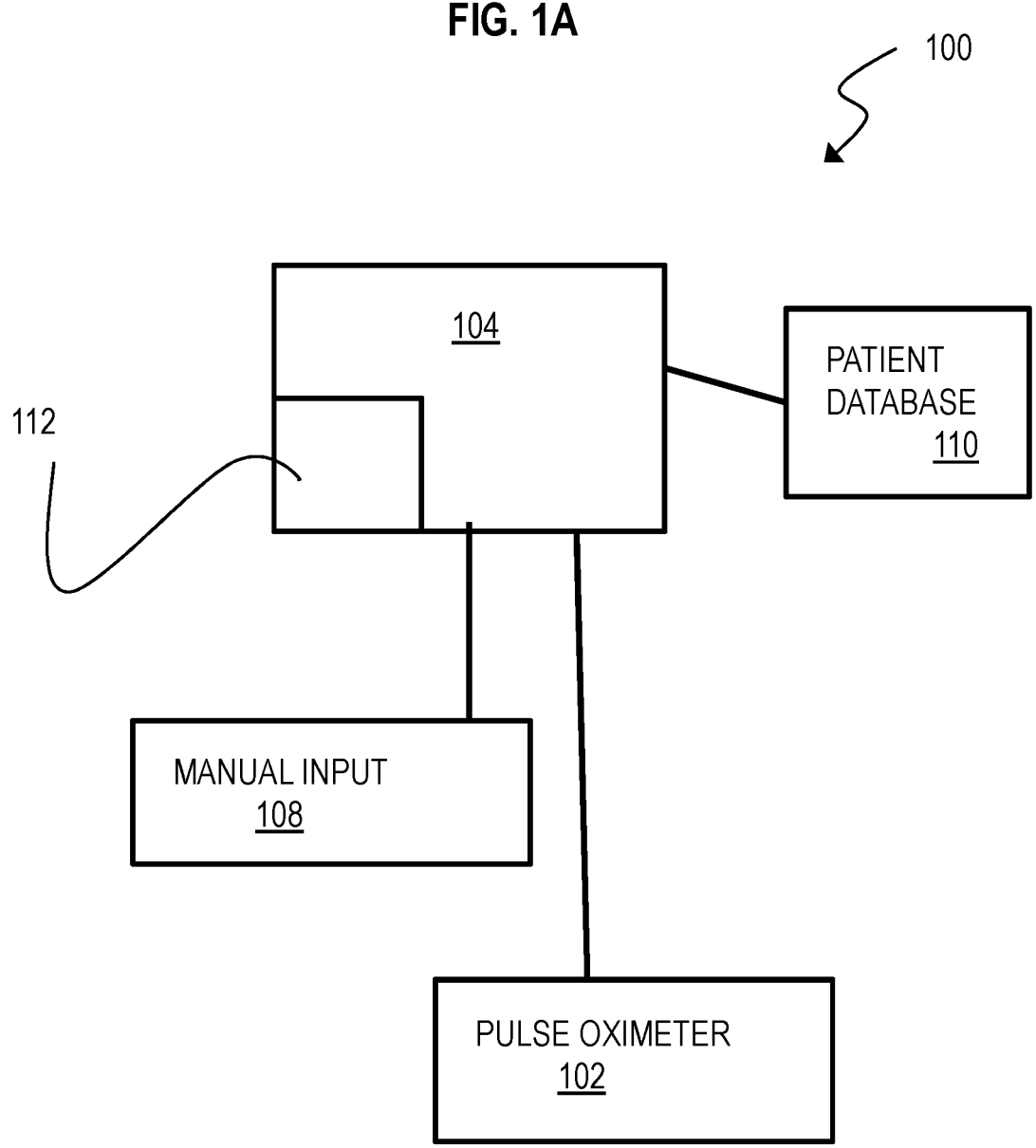
FIG. 1A is a block diagram that illustrates an example of an apparatus for predicting that a patient will require a blood transfusion during a treatment, according to one embodiment.

A method and apparatus are described for predicting that a patient will require a blood transfusion during a treatment. For purposes of the following description, a blood transfusion is defined as an instance in which a patient requires at least one unit of packed red blood cells (pRBC). One unit of pRBC has a volume of approximately 450 ml. pRBC are red blood cells that have been collected, processed, and stored in bags as blood product units available for blood transfusion purposes. The red blood cells are mixed with an anticoagulant and storage solution which provides nutrients and aims to preserve the viability and functionality of the cells, which are stored at refrigerated temperatures. Additionally, a method and apparatus are described for predicting that a patient will require a massive blood transfusion. For purposes of the following description, a massive blood transfusion is defined as an instance in which a patient requires at least five units of pRBC. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of the treatment of patients at a medical facility including an emergency treatment vehicle. However, the invention is not limited to this context. In other embodiments, such as post-injury health care monitoring, detecting unexpected internal bleeding, and ruling out patients with internal bleeding in the field, the invention may be utilized.

1. Overview

When a patient suffers trauma, the first responders attend to the patient and begin treatment, often in the field or in an emergency response vehicle. This treatment often includes attaching vital signs monitors, such as a blood pressure sensor to measure blood pressure and a PPG sensor to measure oxygen saturation of the blood. According to various embodiments the data from one or more of these sensors are used to determine blood loss, even due to hidden internal bleeding, and thus the probability of the need for a transfusion, including need for a massive transfusion. In particular embodiments, the details of the PPG signal are exploited new ways to make an enhanced prediction of the need for blood transfusion.

A blood-oxygen monitor, such as a pulse oximeter, measures a percentage of a patient's blood that is loaded with oxygen. More specifically, the pulse oximeter measures what percentage of hemoglobin (the protein in blood that carries oxygen) is loaded with oxygen. Acceptable ranges for patients without pulmonary pathology are from 95 to 99 percent. Pulse oximetry is a particularly convenient noninvasive measurement method. Typically, the pulse oximeter includes a processor and a pair of small light-emitting diodes (LEDs) facing a photodiode through a translucent part of the patient's body, usually a fingertip or an earlobe. One LED emits red light, with wavelength of about 660 nm, and the other LED emits infrared radiation, with a wavelength of about 940 nm. Absorption of light at these wavelengths differs significantly between blood loaded with oxygen and blood lacking oxygen. The changing absorption at each wavelength is measured during a pressure pulse of a cardiac cycle, allowing determination of the absorbances due to the pulsing arterial blood alone, excluding venous blood, skin, bone, muscle, fat and nail polish. The ratio of the red light measurement to the infrared light measurement is then calculated (which represents the ratio of oxygenated hemoglobin to deoxygenated hemoglobin), and this ratio is then converted to a percentage of $SpO_2$ by the processor via a lookup table. The pulse oximeter also uses the absorption data at each wavelength to determine a variation in blood volume in the skin caused by the pressure pulse during each cardiac cycle. The pulse oximeter generates the PPG waveform based on the variation in the blood volume over time and determines the pulse or heart rate (HR) of the patient based on the time gap between the peaks in the amplitude of the PPG waveform.

FIG. 1A is a block diagram that illustrates an example of a system 100 for predicting whether a patient will require a blood transfusion during a treatment, according to one embodiment. As illustrated in FIG. 1A, a system 100 includes a pulse oximeter 102 configured to measure first data that indicates values for one or more parameters of a characteristic of a continuous photoplethysmographic (PPG) waveform collected during a treatment of a patient. Although the pulse oximeter 102 is depicted in FIG. 1A, any device may be used that is capable of measuring first data that indicates values for one or more parameters of the characteristic of the continuous PPG waveform, as appreciated by one skilled in the art.

As further illustrated in FIG. 1A, the system 100 includes a data processing system 104 connected to the pulse oximeter 102, to receive the first data of the one or more parameters of the PPG waveform. The data processing system 104 includes a process 112 to predict whether the patient will require blood transfusion during the treatment. In some embodiments, the data processing system 104 is a computer system as described below with reference to FIG. 4 or a chip set described below with reference to FIG. 5. The process 112 is configured to cause the system 100 to apply coefficients to the values of the one or more parameters of the PPG waveform and to determine second data that indicates a prediction that the patient will require the blood transfusion during the treatment based on applying the coefficients to the values of the one or more parameters. In one embodiment, the process 112 causes the system 100 to order one or more blood units, based on the prediction. However, the process 112 and the sequence of instructions need not be configured to cause the system 100 to order one or more blood units. The hardware used to form the data processing system 104 of the system 100 is described in more detail below in the Hardware Overview section.

In addition to the first data values of the one or more parameters of the characteristic of the PPG waveform, the data processing system 104 may receive third data that indicates values for one or more secondary parameters of a characteristic of the patient, such as an age and a gender of the patient, for example. FIG. 1A illustrates that the system 100 may include a manual input 108 such as a keyboard or a touchscreen, for example, to manually enter the age and/or gender of the patient whose first data is sent to the data processing system 104 from the pulse oximeter 102. Alternatively, FIG. 1A illustrates the system 100 may include a patient database 110 connected to the data processing system 104 such that the data processing system 104 may automatically retrieve the age and/or gender of the patient whose first data is sent to the data processing system 104 from the pulse oximeter 102. In one embodiment, the sequence of instructions of the process 112 may be configured to, with the data processing system 104, further cause the system 100 to apply coefficients to the values of the one or more secondary parameters of the patient and to further determine the second data that indicates the prediction that the patient will require the blood transfusion during the treatment based on applying the coefficients to the values of the one or more secondary parameters. However, the process 112 may be configured to, with the data processing system 104, cause the system 100 to determine the prediction based on merely applying the coefficients to the values of the first data of the one or more parameters of the characteristic of the PPG waveform.

FIG. 2 is a flow diagram that illustrates an example of a method 200 for predicting that a patient will require a blood transfusion during a treatment, according to one embodiment. Although the flow diagram of FIG. 2, and subsequent flow diagram FIG. 3A, is each depicted as integral steps in a particular order for purposes of illustration, in other embodiments one or more steps, or portions thereof, are performed in a different order, or overlapping in time, in series or in parallel, or are deleted, or one or more other steps are added, or the method is changed in some combination of ways.

After starting at block 201, in step 202, first data is obtained, on the data processing system 104, that indicates values for one or more parameters of a characteristic of a PPG waveform collected during the treatment of the patient. In step 204, coefficients are applied, on the data processing system 104, to the values for the one or more parameters. In step 206, a prediction is determined, on the data processing system 104, that the patient will require a blood transfusion during the treatment. In step 208, a determination is made, on the data processing system 104, on whether to order one or more blood units, based on the prediction, before the method ends at block 209.

Figure 1B:
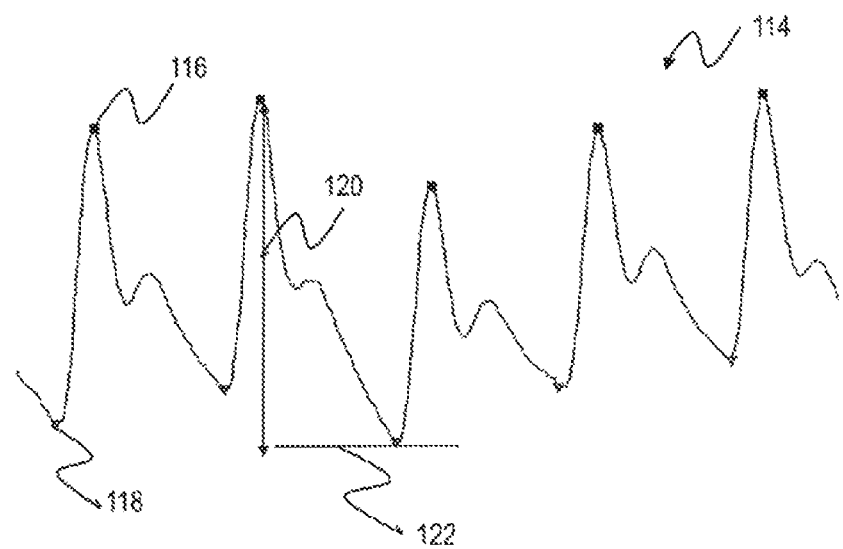
FIG. 1B illustrates an example of a PPG waveform amplitude and period, according to one embodiment.

In one embodiment, the first data values of the one or more parameters are collected over a fixed time interval and the characteristic of the PPG waveform is one or more of a heart rate (HR) and an oxygen saturation ($SpO_2$). FIG. 1B illustrates an example of a PPG waveform 114 including a peak 116, a valley 118 and an amplitude 120 that is measured between consecutive peaks and valleys 116, 118. Additionally, FIG. 1B illustrates that the heart rate 122 is measured based on the time between the peaks 116. As further illustrated in FIG. 1B, the amplitude 120 and heart rate 122 of the PPG waveform 114 varies with time. Thus, over the fixed time interval, a histogram of the amplitude 120 can be made to describe the variability of the amplitude 120 during the fixed time interval. Additionally, over the fixed time interval, a histogram of the heart rate 122 can be made to describe the variability of the heart rate 122 during the fixed time interval.

In another embodiment, the parameters include one or more of a percentage of the fixed time interval that the heart rate is below a threshold heart rate ("% time for HR<threshold"), a percentage of the fixed time interval that the oxygen saturation is below a threshold saturation rate ("% time for $SpO_2$<threshold"), a first percentile of the oxygen saturation over the fixed time interval ("first percentile $SpO_2$") and a second percentile of the oxygen saturation over the fixed time interval that is greater than the first percentile ("second percentile $SpO_2$"). In another embodiment, the parameter includes a percentile of an amplitude of the PPG waveform collected over the fixed time interval ("percentile PPG").

Figure 1C:
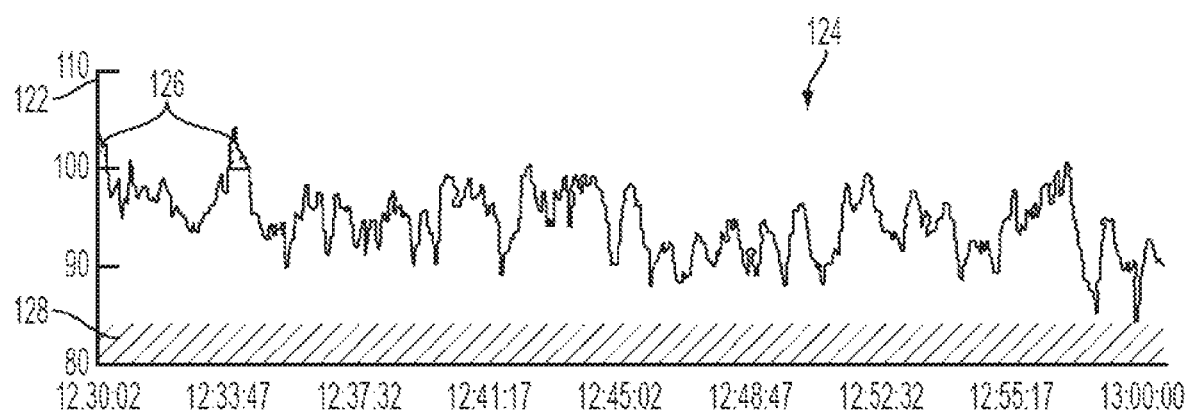
FIG. 1C illustrates an example of a PPG heart rate waveform, according to one embodiment.
Figure 1D:
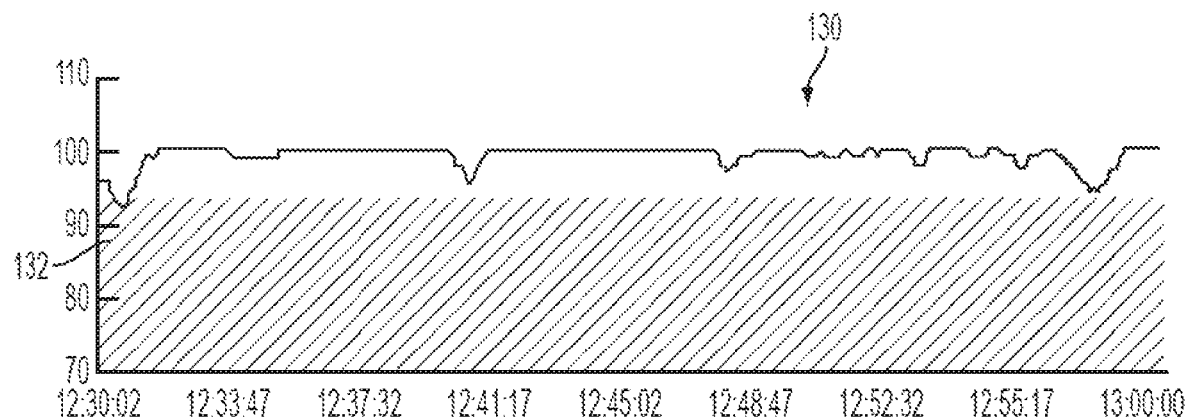
FIG. 1D illustrates an example of a PPG oxygen saturation waveform, according to one embodiment.

In one embodiment, as illustrated in FIG. 1B, the pulse oximeter 102 generates the PPG waveform 114; and illustrated in FIG. 1C a heart rate waveform 124 and in FIG. 1D, an oxygen saturation waveform 130. The heart rate waveform 124 depicts the heart rate 122 (distance between the peaks 116 of the PPG waveform 114) versus time, and the oxygen saturation waveform 130 depicts the percentage of $SpO_2$ in the blood versus time. In the embodiment, the parameter includes one or more of an area 128 of the heart rate waveform 124 below a low threshold heart rate or an area 126 above a high threshold heart rate and an area 132 of the oxygen saturation waveform 130 below a threshold oxygen saturation rate. In the example embodiment of FIG. 1B, the area 128 is based on a low threshold heart rate of about 72 beats per minute, the area 126 is based on a high threshold heart rate of about 100 beats per minute and the area 132 is based on a threshold oxygen saturation rate of about 92%. However, the areas 126, 128, 132 may be based on any threshold rate of the heart rate and oxygen saturation.

In one embodiment, the prediction is based on a time range after the collection of the first data during which the patient will require the blood transfusion. The one or more parameters of the characteristic of the PPG waveform and the coefficients for the one or more parameters that are used to determine the prediction are based on the time range.

FIG. 3A a block diagram that illustrates an example of a method 300 for determining a model for predicting whether a patient will require a blood transfusion, according to one embodiment.

After starting at block 301, in step 302, data is obtained, on the data processing system 104, that indicates values for one or more parameters of a characteristic of a continuous PPG waveform during treatment of a plurality of patients. In step 304, a result is assigned, on the data processing system 104, for each patient based on whether the patient received a blood transfusion during the treatment. In step 306, the data is fitted, on the data processing system 104, to the results for the plurality of patients. In step 308, the coefficients are determined, on the data processing system 104, for the one or more parameters, to determine a model for predicting whether a patient will require a blood transfusion based on an input of the one or more parameters, before the method ends at block 309.

In one embodiment, in step 304, the result is assigned for each patient during a plurality of time ranges of the treatment based on whether each patient received a blood transfusion during each of the time ranges. For example, the result is 1 if a patient receives a transfusion and zero if not. In some embodiments, the result is the number of units of blood the patient received. In the embodiment, in step 306, the data is fitted to each respective result for the plurality of patients during the plurality of time ranges. In the embodiment, in step 308, the coefficients are determined for the one or more parameters for each of the plurality of time ranges, to determine a model for predicting whether a patient will require a blood transfusion during each of the plurality of time ranges based on an input of one or more parameters.

2. Example Embodiments

According to an example embodiment, the first data values of the one or more parameters are collected over one or more fixed time intervals, such as 15 minutes, 30 minutes and/or 60 minutes, for example. According to another example embodiment, the parameters include one or more of a percentage of the fixed time interval that the heart rate is below a threshold heart rate of about 60 beats per minute, a percentage of the fixed time interval that the oxygen saturation is below a threshold saturation rate of about 95%, a first percentile of about 25 percentile of the oxygen saturation over the fixed time interval and/or a second percentile of about 50 percentile of the oxygen saturation over the fixed time interval.

In an example embodiment, a plurality of predictions are determined, based on whether the patient will require a blood transfusion during each of a plurality of time ranges after the collection of the first data, such as within 3 hours, within 6 hours, within 12 hours and within 24 hours after the collection of the first data.

TABLE 1

| | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 1 | Age | −0.018-0.014 | −0.002 | −0.022-0.01 | −0.004 | −0.02-0.012 | −0.002 | −0.01-0.02 | 0.005 |
| 2 | Sex | 0.436-1.964 | 1.151 | 0.55-2.25 | 1.337 | 0.18-1.45 | 0.784 | 0.31-1.59 | 0.918 |
| 3 | PreH-HR | −0.044-0.008 | −0.026 | −0.0--0.012 | −0.03 | −0.04--0.008 | −0.023 | −0.044--0.02 | −0.03 |
| 4 | 10 percentile PPG | −0.005--0.001 | −0.003 | −0.01--0.004 | −0.008 | −0.005--0.002 | −0.003 | | |
| 5 | 20 percentile PPG | | | | | | | −0.03--0.008 | −0.018 |
| 6 | 30 percentile PPG | | | | | | | 0.006-0.03 | 0.017 |
| 7 | 40 percentile PPG | | | 0.002-0.011 | 0.007 | | | | |
| 8 | 50 percentile PPG | | | | | | | | |
| 9 | 60 percentile PPG | | | | | | | | |
| 10 | 70 percentile PPG | | | | | | | | |
| 11 | 80 percentile PPG | | | | | | | | |
| 12 | 90 percentile PPG | | | −0.006--0.0003 | −0.003 | | | −0.004-0.0002 | −0.002 |
| 13 | 25 percentile PPG | | | | | | | | |
| 14 | 75 percentile PPG | | | | | | | | |
| 15 | 25-75 percentile PPG | | | | | | | | |
| 16 | % time for SPO2 <98% | | | | | | | | |
| 17 | Dose for SPO2 <98% | | | | | | | | |
| 18 | % time for SPO2 <95% | 0.052-3.450 | 1.806 | −0.63-3.10 | 1.30 | | | 0.41-3.82 | 2.154 |
| 19 | Dose for SPO2 <95% | 0.059-0.367 | 0.211 | | | 0.041-0.265 | 0.147 | 0.07-0.40 | 0.233 |
| 20 | % time for SPO2 <92% | | | | | | | | |
| 21 | Dose for SPO2 <92% | | | | | | | | |
| 22 | % time for SPO2 <90% | | | | | | | | |
| 23 | Dose for SPO2 <90% | | | | | | | | |
| 24 | % time for SP02 <86% | | | 2.45-9.45 | 5.801 | | | | |
| 25 | Dose for SPO2 <86% | | | | | | | | |
| 26 | 25 percentile SPO2 | 0.329-2.677 | 1.492 | 0.41-2.94 | 1.65 | −0.11-1.72 | 0.814 | | |
| 27 | 50 percentile SPO2 | 0.038-2.114 | 1.085 | 0.005-2.19 | 1.105 | −0.05-1.81 | 0.89 | | |
| 28 | 75 percentile SPO2 | | | | | | | | |
| 29 | mean SP02 | | | | | | | | |
| 30 | % time for HR >120 | | | | | | | | |
| 31 | Dose for HR >120 | | | | | | | | |
| 32 | % time for HR >110 | −0.094-0.01 | −0.04 | −0.11-0.001 | −0.05 | | | | |
| 33 | Dose for HR >110 | | | | | | | | |
| 34 | % time for HR >100 | | | | | | | | |
| 35 | Dose for HR >100 | | | | | | | | 0.008-0.34 | 0.176 |
| 36 | % time for HR <72 | | | | | | | | |
| 37 | Dose for HR <72 | 0.045-0.421 | 0.232 | 0.036-0.417 | 0.225 | | | | |
| 38 | % time for HR <60 | 0.844-4.973 | 2.86 | 0.849-5.182 | 2.96 | 0.41-2.80 | 1.608 | 1.11-3.31 | 2.224 |
| 39 | Dose for HR <60 | | | | | | | | |
| 40 | 25 percentile HR | | | | | | | | |
| 41 | 50 percentile HR | | | | | | | | |
| 42 | 75 percentile HR | | | | | | | | |
| 43 | mean HR | | | | | | | | |
| 44 | Intercept | −43.4-4.95 | −24.14 | −41.91--2.72 | −22.22 | −1.94-1.77 | −0.085 | −34.2-0.143 | −17.05 |
| 45 | Thresholds Range | 0.5-1.0 | 0.5 | 0.5-1.0 | 0.5 | 0.5-1.0 | 0.5 | 0.5-1.0 | 0.5 |

Table 1 provides a list of one or more parameters that are used to determine the prediction, and a 95% confidence interval range of the coefficients for the parameters for each time range, to determine the prediction for each time range. Additionally, Table 1 also provides a list of the recommended coefficient values within the coefficient interval ranges, for each parameter. Blank entries in Table 1 represent zero value coefficients, and thus parameters that are not deemed useful in the model. The coefficient ranges of the parameters listed in Table 1 are based on the first data collection over a fixed time interval of about 15 minutes. Table 2 is also provided, which lists the range of coefficient values and the recommended coefficient values for each parameter, based on the first data being collection over a fixed time interval of about 30 minutes. Similarly, Table 3 is also provided, which lists the range of coefficient values and the recommended coefficient values for each parameter, based on the first data being collection over a fixed time interval of about 60 minutes. The parameters listed in Tables 1-3 are discussed here. The age and gender parameters of the patient were previously discussed and may be manually or automatically input into the data processing system 104. In an example embodiment, the gender parameter may be input numerically as 0 for female and 1 for male. The pre-hospital heart rate ("PreH-HR") parameter is a measure of the patient's heart rate prior to the arrival at the hospital or medical facility and is performed prior to the measurement of the patient's heart rate with the pulse oximeter 102.

TABLE 2

| | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 1 | Age | −0.024-0.014 | −0.004 | −0.018-0.018 | −4.8E−06 | −0.017-0.014 | −0.0014 | −0.009-0.021 | 0.006 |
| 2 | Sex | 0.217-2.034 | 1.057 | 0.434-2.09 | 1.204 | 0.273-1.618 | 0.910 | 0.289-1.611 | 0.917 |
| 3 | PreH-HR | −0.04--0.005 | −0.025 | −0.04--0.006 | −0.023 | −0.043--0.013 | −0.028 | −0.042--0.011 | −0.027 |
| 4 | 10 percentile PPG | −0.006--0.002 | −0.004 | −0.009--0.0035 | −0.0065 | −0.005--0.0013 | −0.003 | −0.0044--0.001 | −0.0027 |
| 5 | 20 percentile PPG | | | | | | | | |
| 6 | 30 percentile PPG | | | | | | | | |
| 7 | 40 percentile PPG | | | | | | | | |
| 8 | 50 percentile PPG | | | | | | | | |
| 9 | 60 percentile PPG | | | | | | | | |
| 10 | 70 percentile PPG | | | | | | | | |
| 11 | 80 percentile PPG | | | | | | | | |
| 12 | 90 percentile PPG | | | −0.014--0.002 | −0.008 | | | | |
| 13 | 25 percentile PPG | | | | | | | | |
| 14 | 75 percentile PPG | | | | | | | | |
| 15 | 25-75 percentile PPG | | | | | | | | |
| 16 | % time for SPO2 <98% | | | | | | | | |
| 17 | Dose for SPO2 <98% | | | | | | | | |
| 18 | % time for SPO2 <95% | | | | | | | | −0.736-3.143 | 1.285 |
| 19 | Dose for SPO2 <95% | | | | | | | | |
| 20 | % time for SPO2 <92% | | | | | | | | |
| 21 | Dose for SPO2 <92% | | | | | | | | |
| 22 | % time for SPO2 <90% | | | | | | | | |
| 23 | Dose for SPO2 <90% | | | −0.674-0.103 | −0.272 | | | | |
| 24 | % time for SPO2 <86% | 3.819-14.01 | 8.79 | 6.016-23.175 | 14.34 | 4.57-13.09 | 8.71 | 3.846-12.615 | 8.04 |
| 25 | Dose for SPO2 <86% | | | | | | | | |
| 26 | 25 percentile SPO2 | | | 0.684-4.17 | 2.382 | | | | |
| 27 | 50 percentile SPO2 | | | | | | | 0.650-3.317 | 1.965 |
| 28 | 75 percentile SPO2 | | | −0.395-7.158 | 3.435 | | | | |
| 29 | mean SP02 | −15.34-2.05 | −6.63 | | | −10.97-1.111 | −4.98 | | |
| 30 | % time for HR >120 | | | | | | | | |
| 31 | Dose for HR >120 | | | | | | | | |
| 32 | % time for HR >110 | 0.007-1.029 | 0.516 | | | 0.034-0.70 | 0.371 | | |
| 33 | Dose for HR >110 | | | | | | | | |
| 34 | % time for HR >100 | | | | | | | | |
| 35 | Dose for HR >100 | | | | | | | | |
| 36 | % time for HR <72 | | | −1.694--0.15 | −0.853 | | | | |
| 37 | Dose for HR <72 | 0.186-0.698 | 0.427 | 0.147-0.591 | 0.362 | 0.136-0.538 | 0.330 | 0.112-0.551 | 0.333 |
| 38 | % time for HR <60 | | | 0.241-3.788 | 2.03 | | | | |
| 39 | Dose for HR <60 | −1.07--0.025 | −0.547 | | | −0.727--0.242 | −0.381 | −0.148-0.14 | −0.062 |
| 40 | 25 percentile HR | −0.08-0.002 | −0.04 | −0.088-0.006 | −0.041 | | | | |
| 41 | 50 percentile HR | | | | | | | | |
| 42 | 75 percentile HR | −0.008-0.057 | 0.025 | | | | | 0.029-0.0823 | 0.055 |
| 43 | mean HR | | | | | | | | |
| 44 | Intercept | −69.86--17.38 | −42.08 | −56.65--10.68 | −32.94 | −53.60--12.97 | −32.61 | −61.13--16.04 | −38.69 |
| 45 | Thresholds Range | 0.5-1.0 | 0.5 | 0.5-1.0 | 0.5 | 0.5-1.0 | 0.5 | 0.5-1.0 | 0.5 |

TABLE 3

| | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 1 | Age | −0.022-0.014 | −0.004 | −0.023-0.011 | −0.0057 | −0.019-0.011 | −0.004 | −0.011-0.018 | 0.0033 |
| 2 | Sex | 0.323-2.073 | 1.134 | 0.402-1.950 | 1.126 | 0.231-1.552 | 0.860 | 0.289-1.611 | 0.917 |
| 3 | PreH-HR | −0.044--0.008 | −0.026 | −0.041--0.008 | −0.0245 | −0.039--0.009 | −0.024 | −0.042--0.011 | −0.027 |

TABLE 3-continued

| Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|
| 4 10 percentile PPG | −0.007-0.0026 | −0.0047 | −0.007−−0.003 | −0.0049 | −0.006−−0.0025 | −0.004 | −0.0044−−0.001 | −0.0027 |
| 5 20 percentile PPG | | | | | | | | |
| 6 30 percentile PPG | | | | | | | | |
| 7 40 percentile PPG | | | | | | | | |
| 8 50 percentile PPG | | | | | | | | |
| 9 60 percentile PPG | | | | | | | | |
| 10 70 percentile PPG | | | | | | | | |
| 11 80 percentile PPG | | | | | | | | |
| 12 90 percentile PPG | | | | | | | | |
| 13 25 percentile PPG | | | | | | | | |
| 14 75 percentile PPG | | | | | | | | |
| 15 25-75 percentile PPG | | | | | | | | |
| 16 % time for SPO2 <98% | | | | | | | | |
| 17 Dose for SPO2 <98% | | | | | | | | |
| 18 % time for SPO2 <95% | | | | | | | −0.736-3.143 | 1.285 |
| 19 Dose for SPO2 <95% | | | | | | | | |
| 20 % time for SPO2 <92% | | | | | | | | |
| 21 Dose for SPO2 <92% | | | −1.07−−0.080 | −0.550 | | | | |
| 22 % time for SPO2 <90% | | | | | | | | |
| 23 Dose for SPO2 <90% | | | | | −0.936−−0.259 | −0.461 | | |
| 24 % time for SPO2 <86% | 7.618-27.77 | 17.26 | 11.16-35.25 | 22.70 | 9.094-29.37 | 18.93 | 3.846-12.615 | 8.04 |
| 25 Dose for SPO2 <86% | | | | | | | | |
| 26 25 percentile SPO2 | | | | | | | | |
| 27 50 percentile SPO2 | | | | | | | 0.650-3.317 | 1.965 |
| 28 75 percentile SPO2 | | | | | | | | |
| 29 mean SP02 | 1.274-3.80 | 2.55 | | | | | | |
| 30 % time for HR >120 | | | −0.278-0.042 | −0.120 | −0.265-0.034 | −0.116 | | |
| 31 Dose for HR >120 | −0.033-0.570 | 0.259 | | | | | | |
| 32 % time for HR >110 | | | 0.025-0.280 | 0.153 | 0.025-0.260 | 0.143 | | |
| 33 Dose for HR >110 | | | | | | | | |
| 34 % time for HR >100 | | | | | | | | |
| 35 Dose for HR >100 | | | 0.114-0.460 | 0.281 | 0.107-0.426 | 0.262 | | |
| 36 % time for HR <72 | | | | | | | | |
| 37 Dose for HR <72 | 0.088-0.655 | 0.373 | | | | | 0.112-0.551 | 0.333 |
| 38 % time for HR <60 | | | | | | | | |
| 39 Dose for HR <60 | | | | | | | −0.148-0.14 | −0.062 |
| 40 25 percentile HR | | | | | | | | |
| 41 50 percentile HR | | | | | | | | |
| 42 75 percentile HR | | | | | | | 0.029-0.0823 | 0.055 |
| 43 mean HR | | | | | | | | |
| 44 Intercept | −99.40−−29.89 | −62.66 | −45.23−−10.69 | −27.44 | −41.91−−9.83 | −25.40 | −61.13−−16.04 | −38.69 |
| 45 Thresholds Range | 0.5-1.0 | 0.5 | 0.5-1.0 | 0.5 | 0.5-1.0 | 0.5 | 0.5-1.0 | 0.5 |

Additional parameters include one or more percentiles of an amplitude of the PPG waveform ("percentile PPG") over the fixed time interval. The amplitude percentiles may be determined by the data processing system 104 based on the received first data or determined by the pulse oximeter 102 and subsequently transmitted to the data processing system 104. The percentiles of the amplitude of the PPG waveform may be one or more of 10 percentile, 20 percentile, 30 percentile, 40 percentile, 50 percentile, 60 percentile, 70 percentile, 80 percentile, 90 percentile, 25 percentile, 75 percentile and a difference between the 25 and 75 percentile.

Additional parameters include a percentage of the fixed time interval that the oxygen saturation is below a threshold saturation rate, such as about 98%, 95%, 92%, 90% and 86% ("% time for SpO2").

Additional parameters include an area of the oxygen saturation waveform below the threshold saturation rates ("Dose for SpO2"). Additional parameters include a 25 percentile, a 50 percentile, a 75 percentile and a mean of the oxygen saturation level during the fixed time interval. For example, the 25 percentile of the oxygen saturation level may be that, during 25% of the fixed time interval, the oxygen saturation was at a level of 98% or higher.

Additional parameters include a percentage of the fixed time interval that the heart rate is below a low threshold heart rate, such as about 60 beats per minute or 72 beats per minute, or above a high threshold heart rate, such as about 100 beats per minute, 110 beats per minute or 120 beats per minute ("% time for HR"). Additional parameters include an area of the heart rate waveform below the low threshold heart rate or above the high threshold heart rate ("Dose for HR"). Additional parameters include a 25 percentile, a 50 percentile, a 75 percentile and a mean of the heart rate level during the fixed time interval. For example, the 25 percentile of the heart rate level may be that, during 25% of the fixed time interval, the heart rate was at a level of 100 beats per minute or higher.

The coefficient ranges listed in Table 1 encompass all coefficient values and coefficient ranges that are within the listed ranges in Table 1. The parameters that may be used to determine the prediction are not limited to those parameters listed in Table 1 and include any parameter that is derived from a characteristic of the PPG waveform or an identifying characteristic of the patient. Additionally, the ranges of the coefficients for the parameters listed in Table 1 are not limited to the specific numerical ranges listed in Table 1.

Table 1 lists a range for an intercept that is used to form the equation for determining the prediction for each time range. The formula for the prediction (P) for each time range is based on the following equation:

$$P = C_1 * V_1 + C_2 * V_2 + \ldots + I$$

Where $V_1$ is the first value of a first parameter, $V_2$ is the second value of a second parameter, and $C_1$ and $C_2$ are the respective first and second coefficients for the first and second parameters, based on Table 1. Additionally, I is the intercept for the specific time range within which the prediction P is being made, based on Table 1. Although the prediction (P) formula above merely lists two values for two parameters and two coefficients, less or more than two parameters and two coefficients may be used to determine the prediction.

As shown in Table 1, for the time range of up to 3 hours after the collection of the first data, the coefficient range for the percentage of the fixed time interval that the heart rate is below the threshold heart rate of about 60 beats per minute is in a range from about 0.84 to about 4.93. Additionally, the coefficient range for the percentage of the fixed time interval that the oxygen saturation is below the threshold saturation rate of about 95% is in a range from about 0.05 to about 3.45. Additionally, the coefficient range for the 25 percentile of the oxygen saturation is in a range from about 0.33 to about 2.68 and the coefficient for the 50 percentile of the oxygen saturation is in a range from about 0.04 to about 2.11. In an example embodiment, the above parameters with the largest magnitude coefficients may be used to determine the prediction for the time range of up to 3 hours after the collection of the first data. However, fewer or more than the above listed parameters may be used to determine the prediction.

As shown in Table 1, for the time range of up to 6 hours after the collection of the first data, the coefficient range for the percentage of the fixed time interval that the heart rate is below the threshold heart rate of about 60 beats per minute is in a range from about 0.85 to about 5.18. Additionally, the coefficient range for the percentage of the fixed time interval that the oxygen saturation is below the threshold saturation rate of about 86% is in a range from about 2.45 to about 9.45. Additionally, the coefficient range for the 25 percentile of the oxygen saturation is in a range from about 0.41 to about 2.93 and the coefficient for the 50 percentile of the oxygen saturation is in a range from about 0.01 to about 2.20. In an example embodiment, the above parameters with the largest magnitude coefficients may be used to determine the prediction of whether the patient will require the blood transfusion within 6 hours after the collection of the first data. However, fewer or more than the above listed parameters may be used to determine the prediction.

As shown in Table 1, for the time range of up to 12 hours after the collection of the first data, the coefficient range for the percentage of the fixed time interval that the heart rate is below the threshold heart rate of about 60 beats per minute is in a range from about 0.41 to about 2.80. Additionally, the coefficient range for the percentage of the fixed time interval that the oxygen saturation is below the threshold saturation rate of about 95% is in a range from about 0.04 to about 0.26. Additionally, the coefficient range for the 25 percentile of the oxygen saturation is in a range from about −0.11 to about 1.72 and the coefficient for the 50 percentile of the oxygen saturation is in a range from about −0.05 to about 1.81. In an example embodiment, the above parameters with the largest magnitude coefficients may be used to determine the prediction of whether the patient will require the blood transfusion within 12 hours after the collection of the first data. However, less or more than the above listed parameters may be used to determine the prediction.

As shown in Table 1, for the time range of up to 24 hours after the collection of the first data, the coefficient range for the percentage of the fixed time interval that the heart rate is below the threshold heart rate of about 60 beats per minute is in a range from about 1.11 to about 3.31. Additionally, the coefficient range for the percentage of the fixed time interval that the oxygen saturation is below the threshold saturation rate of about 95% is in a range from about 0.41 to about 3.82. In an example embodiment, the above parameters with the largest magnitude coefficients may be used to determine the prediction of whether the patient will require the blood transfusion within 24 hours after the collection of the first data. However, less or more than the above listed parameters may be used to determine the prediction.

Additionally, as shown in Table 1, for the prediction determination within each time range, a threshold range for the prediction is about 0.5-1.0. Thus, if the calculated prediction (P) is above 0.5, the patient is likely in need of a transfusion within the time range. If the calculated prediction is between 0.2 and 0.5, then further investigation, such as further collection of the first data, may be necessary. If the calculated prediction is below 0.2, then the patient is likely not in need of a transfusion within the time range after the collection of the first data. In an example embodiment, the data processing system 104 may include a display to output the prediction and/or may transmit a signal to a remote location such as a blood bank at a proximate location to the hospital, for example, to order one or more blood units, based on the prediction in excess of 0.5, for example.

In an example embodiment, a plurality of additional predictions are determined, based on whether the patient will require a first massive blood transfusion (MT1) of at least 5 units of pRBC within 4 hours after the collection of the first data; whether the patient will require a second massive blood transfusion (MT2) of at least 10 units of pRBC within 6 hours after the collection of the first data; and whether the patient will require a third massive blood transfusion (MT3) of at least 10 units of pRBC within 24 hours after the collection of the first data. The MT1, MT2 and MT3 predictions are determined in a similar manner as the method for determining the prediction P with the data processing system 104, by applying one or more secondary coefficients for the MT1, MT2 and MT3 predictions to the values for the one or more parameters of the first data. The secondary coefficients for the MT1, MT2 and MT3 predictions are determined in a similar manner as the method for determining the coefficients for the prediction P of whether the patient will require a blood transfusion of one or more blood units.

Table 4 provides a list of one or more parameters that are used to determine the MT1, MT2 and MT3 predictions, and a 95% confidence interval range of secondary coefficients for the parameters for each MT1, MT2 and MT3 prediction. Additionally, Table 4 also provides a list of the recommended secondary coefficient values within the coefficient interval ranges, for each parameter. Blank entries in Table 4 represent zero value secondary coefficients, and thus parameters that are not deemed useful in the model. The secondary coefficient ranges of the parameters listed in Table 4 are based on the first data collection over a fixed time interval of about 15 minutes. Table 5 is also provided, which lists the range of secondary coefficient values and the recommended secondary coefficient values for each parameter, based on the first data being collection over a fixed time interval of about 30 minutes. Similarly, Table 6 is also provided, which lists the range of secondary coefficient values and the recommended secondary coefficient values for each parameter, based on the first data being collection over a fixed time interval of about 60 minutes.

TABLE 4

| Parameter | MT1 (range) | MT1 | MT2 (range) | MT2 | MT3 (range) | MT3 |
|---|---|---|---|---|---|---|
| 1 Age | −0.034-0.02 | −0.006 | −0.032-0.032 | 0.001 | −0.036-0.034 | −0.00001 |
| 2 Sex | 0.035-2.56 | 1.17 | −0.784-2.07 | 0.495 | −0.522-2.471 | 0.804 |
| 3 PreH-HR | | | 0.005-0.58 | 0.032 | 0.005-0.057 | 0.0307 |
| 4 10 percentile PPG | | | | | −0.015-0.0025 | −0.006 |
| 5 20 percentile PPG | −0.007--0.001 | −0.004 | −0.035--0.004 | −0.02 | | |
| 6 30 percentile PPG | | | −0.0015-0.027 | 0.013 | | |
| 7 40 percentile PPG | | | | | −0.037-0.009 | −0.0154 |
| 8 50 percentile PPG | | | | | −0.004-0.033 | 0.0161 |
| 9 60 percentile PPG | | | | | | |
| 10 70 percentile PPG | | | | | | |
| 11 80 percentile PPG | | | | | | |
| 12 90 percentile PPG | | | | | | |
| 13 25 percentile PPG | | | | | | |
| 14 75 percentile PPG | | | | | | |
| 15 25-75 percentile PPG | | | | | | |
| 16 % time for SPO2 <98% | | | | | | |
| 17 Dose for SPO2 <98% | | | | | | |
| 18 % time for SPO2 <95% | | | | | | |
| 19 Dose for SPO2 <95% | | | | | | |
| 20 % time for SPO2 <92% | | | | | | |
| 21 Dose for SPO2 <92% | −1.96--0.142 | −0.88 | | | | |
| 22 % time for SPO2 <90% | | | | | | |
| 23 Dose for SPO2 <90% | | | | | | |
| 24 % time for SP02 <86% | 13.76--48.75 | 28.62 | | | 1.894--11.48 | 7.042 |
| 25 Dose for SPO2 <86% | | | | | | |
| 26 25 percentile SPO2 | | | | | | |
| 27 50 percentile SPO2 | 0.513-4.56 | 2.54 | | | | |
| 28 75 percentile SPO2 | | | −0.207-5.382 | 2.893 | 1.17-6.094 | 3.762 |
| 29 mean SP02 | | | | | | |
| 30 % time for HR >120 | | | | | | |
| 31 Dose for HR >120 | | | | | | |
| 32 % time for HR >110 | | | | | | |
| 33 Dose for HR >110 | | | | | | |
| 34 % time for HR >100 | | | | | | |
| 35 Dose for HR >100 | | | | | | |
| 36 % time for HR <72 | | | | | | |
| 37 Dose for HR <72 | 0.341-1.221 | 0.731 | | | −0.0068-0.5462 | 0.2697 |
| 38 % time for HR <60 | | | | | | |
| 39 Dose for HR <60 | | | | | | |
| 40 25 percentile HR | 0.064-0.272 | 0.142 | | | | |
| 41 50 percentile HR | −0.22--0.03 | −0.10 | | | | |
| 42 75 percentile HR | | | | | | |
| 43 mean HR | | | | | | |
| 44 Intercept | −130.1--39.55 | 79.69 | −10.46--2.25 | 6.127 | −63.43--6.181 | −34.56 |
| 45 Thresholds Range | 0.5-1.0 | 0.5 | 0.5-1.0 | 0.5 | 0.5-1.0 | 0.5 |

TABLE 5

| Parameter | MT1 (range) | MT1 | MT2 (range) | MT2 | MT3 (range) | MT3 |
|---|---|---|---|---|---|---|
| 1 Age | −0.040-0.015 | −0.011 | −0.035-0.030 | −0.0014 | −0.026-0.0344 | 0.0051 |
| 2 Sex | −0.155-2.349 | 0.982 | −0.915-2.081 | 0.438 | −0.665-2.241 | 0.633 |
| 3 PreH-HR | | | 0.0009-0.0053 | 0.0262 | 0.002-0.051 | 0.026 |
| 4 10 percentile PPG | | | | | | |
| 5 20 percentile PPG | | | | | | |
| 6 30 percentile PPG | | | | | | |
| 7 40 percentile PPG | | | | | | |
| 8 50 percentile PPG | | | | | | |
| 9 60 percentile PPG | | | 0.0013-0.011 | 0.0063 | 0.0017-0.011 | 0.0064 |
| 10 70 percentile PPG | | | | | | |
| 11 80 percentile PPG | | | | | | |
| 12 90 percentile PPG | −0.0084--0.0031 | −0.0057 | | | | |
| 13 25 percentile PPG | | | −0.0199--0.0073 | −0.013 | −0.018--0.0069 | −0.012 |
| 14 75 percentile PPG | | | | | | |
| 15 25-75 percentile PPG | 0.0047-0.0137 | 0.009 | | | | |
| 16 % time for SPO2 <98% | | | | | | |
| 17 Dose for SPO2 <98% | −1.10--0.096 | −0.525 | | | | |
| 18 % time for SPO2 <95% | | | | | | |
| 19 Dose for SPO2 <95% | | | | | | |
| 20 % time for SPO2 <92% | | | | | | |
| 21 Dose for SPO2 <92% | | | | | | |
| 22 % time for SPO2 <90% | | | | | | |
| 23 Dose for SPO2 <90% | | | | | | |
| 24 % time for SP02 <86% | 13.07-45.279 | 27.434 | | | | |
| 25 Dose for SPO2 <86% | | | | | | |

TABLE 5-continued

| Parameter | MT1 (range) | MT1 | MT2 (range) | MT2 | MT3 (range) | MT3 |
|---|---|---|---|---|---|---|
| 26 25 percentile SPO2 | | | | | | |
| 27 50 percentile SPO2 | −0.258-2.837 | 1.355 | | | | |
| 28 75 percentile SPO2 | | | | | −0.0943-5.470 | 3.032 |
| 29 mean SP02 | | | | | | |
| 30 % time for HR >120 | | | 0.017-0.127 | 0.0735 | 0.0216-0.125 | 0.0753 |
| 31 Dose for HR >120 | | | | | | |
| 32 % time for HR >110 | 0.0295-0.109 | 0.069 | | | | |
| 33 Dose for HR >110 | | | | | | |
| 34 % time for HR >100 | | | −0.0782-0.231 | 0.106 | | |
| 35 Dose for HR >100 | | | | | | |
| 36 % time for HR <72 | | | | | | |
| 37 Dose for HR <72 | 0.274-1.064 | 0.641 | | | | |
| 38 % time for HR <60 | | | | | | |
| 39 Dose for HR <60 | | | | | | |
| 40 25 percentile HR | | | | | | |
| 41 50 percentile HR | | | | | | |
| 42 75 percentile HR | | | | | | |
| 43 mean HR | | | | | | |
| 44 Intercept | −108.86--28.92 | −66.10 | −10.15--1.54 | −5.60 | −10.65--2.383 | −6.272 |
| 45 Thresholds Range | 0.5-1.0 | 0.5 | 0.5-1.0 | 0.5 | 0.5-1.0 | 0.5 |

TABLE 6

| Parameter | MT1 (range) | MT1 | MT2 (range) | MT2 | MT3 (range) | MT3 |
|---|---|---|---|---|---|---|
| 1 Age | −0.039--0.013 | −0.012 | −0.023--0.045 | 0.012 | −0.039--0.0264 | −0.005 |
| 2 Sex | −0.495--1.803 | 0.573 | −0.927--2.243 | 0.528 | −0.759--2.205 | 0.580 |
| 3 PreH-HR | | | | | | |
| 4 10 percentile PPG | | | | | | |
| 5 20 percentile PPG | −0.056--0.0011 | −0.029 | | | | |
| 6 30 percentile PPG | | | −0.0217--0.0039 | −0.013 | −0.016--0.0021 | −0.0093 |
| 7 40 percentile PPG | | | | | | |
| 8 50 percentile PPG | | | −0.0011--0.0148 | 0.0073 | −0.0018--0.011 | 0.0048 |
| 9 60 percentile PPG | | | | | | |
| 10 70 percentile PPG | | | | | | |
| 11 80 percentile PPG | | | | | | |
| 12 90 percentile PPG | | | | | | |
| 13 25 percentile PPG | −0.0046--0.0469 | 0.0217 | | | | |
| 14 75 percentile PPG | | | | | | |
| 15 25-75 percentile PPG | | | | | | |
| 16 % time for SPO2 <98% | | | | | | |
| 17 Dose for SPO2 <98% | | | | | | |
| 18 % time for SPO2 <95% | | | −59.214--7.71 | −29.07 | | |
| 19 Dose for SPO2 <95% | −1.382--0.146 | −0.754 | | | | |
| 20 % time for SPO2 <92% | | | 22.26--146.45 | 83.05 | | |
| 21 Dose for SPO2 <92% | | | | | −1.321--0.0002 | −0.654 |
| 22 % time for SPO2 <90% | | | −183.31--9.063 | −97.87 | | |
| 23 Dose for SPO2 <90% | | | | | | |
| 24 % time for SP02 <86% | 17.981--56.242 | 36.429 | 15.314--127.45 | 68.18 | 16.317--55.133 | 34.752 |
| 25 Dose for SPO2 <86% | | | | | | |
| 26 25 percentile SPO2 | | | | | | |
| 27 50 percentile SPO2 | −0.426--2.741 | 1.235 | | | | |
| 28 75 percentile SPO2 | | | | | | |
| 29 mean SP02 | | | | | | |
| 30 % time for HR >120 | | | | | | |
| 31 Dose for HR >120 | | | | | | |
| 32 % time for HR >110 | 0.047--0.131 | 0.088 | 0.0428--0.1532 | 0.0957 | 0.053--0.150 | 0.1003 |
| 33 Dose for HR >110 | | | | | | |
| 34 % time for HR >100 | | | | | −0.077--0.199 | 0.0864 |
| 35 Dose for HR >100 | 0.324--0.943 | 0.611 | | | 0.356--1.137 | 0.702 |
| 36 % time for HR <72 | | | | | | |
| 37 Dose for HR <72 | | | 0.9334--5.01 | 2.396 | | |
| 38 % time for HR <60 | | | | | | |
| 39 Dose for HR <60 | | | | | | |
| 40 25 percentile HR | | | | | | |
| 41 50 percentile HR | | | | | | |
| 42 75 percentile HR | | | | | | |
| 43 mean HR | | | | | | |
| 44 Intercept | −96.27--33.90 | −62.87 | −504.37--95.98 | −242.82 | −117.34--38.62 | −73.65 |
| 45 Thresholds Range | 0.5-1.0 | 0.5 | 0.5-1.0 | 0.5 | 0.5-1.0 | 0.5 |

According to an example embodiment, the data processing system 104 obtained data for values of one or more parameters of a characteristic of the continuous PPG waveform during treatment of a plurality of patients. In an example embodiment, a shock index (SI) of at least 0.60 was used to qualify trauma patients for a study. The SI is defined as a ratio of the heart rate (in beats per minute) to the systolic blood pressure (in millimeters of mercury). In an example embodiment, the study was conducted in which 556 trauma patients were enrolled, 37 of those patients received a transfusion within 24 hours, and the data for the parameters listed in Table 1 was obtained for all of the patients over a 24 hour period of treatment. The pulse oximeter 102 was used to measure PPG waveform data including heart rate, oxygen saturation and PPG amplitude data over the fixed time periods, such as 15 minutes, 30 minutes and 60 minutes, for example. The data processing system 104 received the data from the pulse oximeter 102, including the parameters listed in Table 1.

The data processing system 104 assigned a respective result for each patient based on whether the patient received a blood transfusion within the time ranges of 3 hours, 6 hours, 12 hours and 24 hours after the commencement of the collection of the PPG waveform data. In an example embodiment, the processor 204 assigned the result a value of 1.0 if a patient did receive a transfusion in a time range of treatment and assigned the result a value of 0 if the patient did not receive a transfusion during the time range of treatment. In an example embodiment, for each time range, the data processing system 104 fitted the data for the values of the one or more parameters to the results for the patients, using a software package such as MatLab® 3.13 R2011B; MathWorks, Natick, Mass. Based on the fitting of the data for the values of the one or more parameters to the results for the patients, the data processing system 104 determined the coefficients (see Table 1) for the one or more parameters, for each time range, to determine a model for predicting whether a patient will require a blood transfusion within each time range, based on an input of the one or more parameters.

Figure 3B:
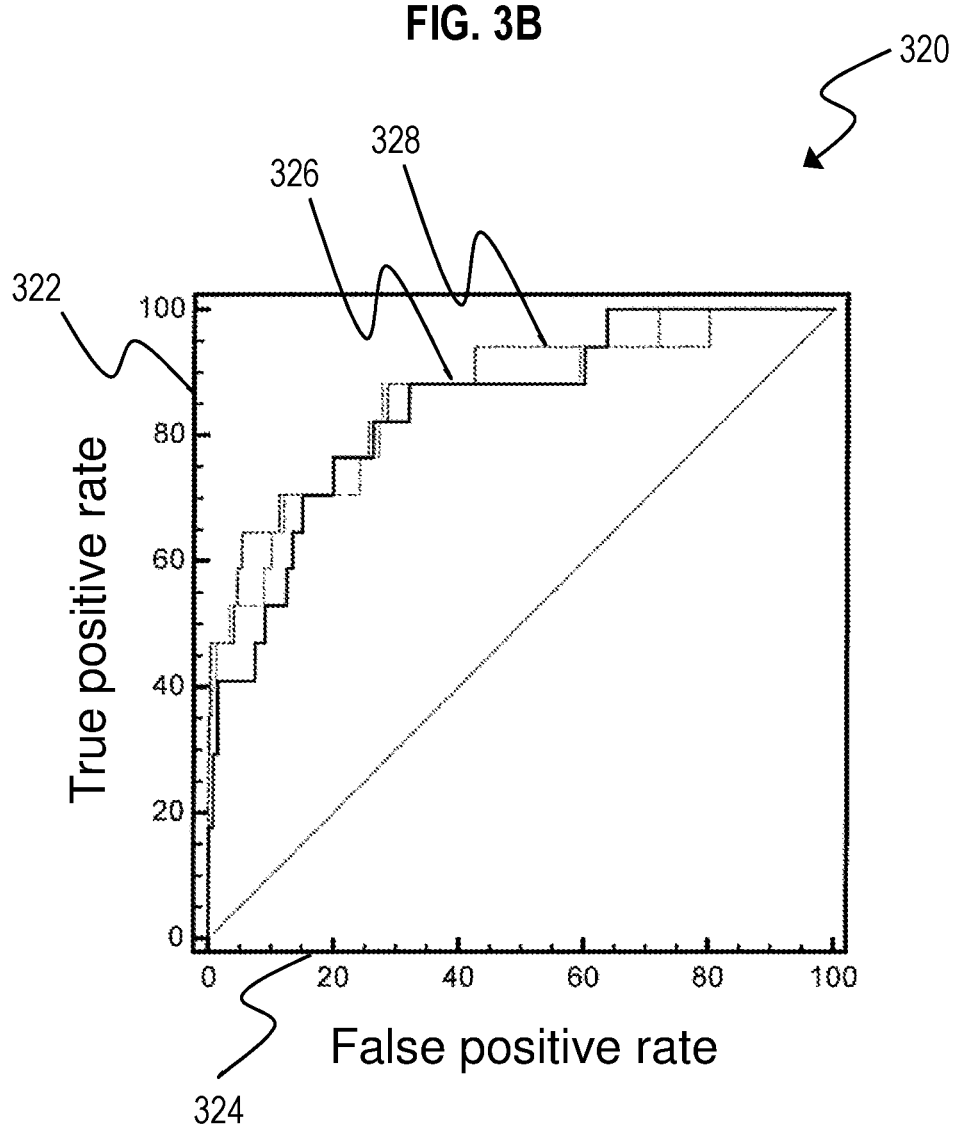
FIG. 3B illustrates an example of a receiver operating characteristic (ROC) curve, according to one embodiment.

To measure the performance of the prediction model, a true positive rate (TPR) is calculated, based on a ratio of the number of patients who needed a transfusion and whose prediction (P) value exceeded the threshold to the total number of patients whose prediction (P) value exceeded the threshold. Additionally, a false positive rate (FPR) is calculated, which is based on a ratio of the number of patients who did not need a transfusion and had a prediction value (P) that exceeded the transfusion threshold to the total number of patients whose prediction (P) value exceeded the transfusion threshold. The TPR and the FPR varies, based on the numerical threshold. FIG. 3B illustrates an example of a receiver operating characteristic (ROC) curve 320, which plots the TPR 322 versus the FPR 324, for a range of transfusion thresholds. As appreciated by one skilled in the art, an area under the ROC curve (AUROC) provides a measure of the performance of the prediction model, where the larger the area (up to 1), the better the performance of the model at predicting whether a patient needs a transfusion. In an example embodiment, the AUROC for the models for predicting whether the patient will require the blood transfusion within 3 hours, 6 hours, 12 hours and 24 hours of the data collection is in a range of 0.80-0.84, in excess of conventional prediction methods based on conventional vital sign (VS) data collection of parameters other than the parameters listed in Table 1. As illustrated in FIG. 3B, a first ROC curve 326 is based on the first data collection over the fixed time interval of 15 minutes and the second ROC curve 328 is based on the first data collection over the fixed time interval of 30 minutes. In an example embodiment, the performance of the prediction model of whether the patient will require the blood transfusion within each time range based on the fixed time interval of 15 minutes of data (AUROC 0.80-0.83) was unexpectedly insignificant to the performance of the prediction model of whether the patient will require the blood transfusion within each time range based on a longer fixed time interval of 30 minutes (AUROC 0.81-0.85) or 60 minutes (0.82-0.85) of data collection.

In an example embodiment, for each of the plurality of patients, continuous vital sign (VS) data is collected from each patient via. Bedmaster® software (Excel Medical Electronics, Jupiter Fla., USA) from networked patient monitors (GE-Marquette Solar 7000/8000, GE® Healthcare) using two VS data collection servers. In an example embodiment, electrocardiogram (ECG) and PPG waveforms were collected at 240 Hz. Heart rate (HR) values (from PPG) and oxygen saturation ($SpO_2$) values were obtained every five seconds (0.2 Hz) from the pulse oximeter 102. The collected data was compressed and transferred to the data processing system 104, such as through an intranet of the hospital facility, for example. In an example embodiment, VS data streaming rate after compression averaged 12 MB/hour for waveforms and 76 Kb/hour for VS data. One hour of continuous VS data and PPG waveform data was collected for analysis, beginning at the time of arrival of the patient at the trauma unit of the hospital. In an example embodiment, blood use was tracked by direct observation of resuscitation and by cross-validation with blood bank records tracking individual blood product unit types and time of release from the blood bank.

In an example embodiment, the data processing system 104 may be configured to filter the collected first data based on a PPG signal quality index (PPG-SQI). The SQI is used to identify segments of the PPG waveform when there was agreement between a pulse oximeter monitor pulse rate reading ($PR_1$) and an automated PPG measurement of peak-to-peak distance ($PR_2$).

$$\text{If } \frac{PR_1 - PR_2}{0.5 * (PR_1 + PR_2)} > 5\%,$$

then the segment of the PPG waveform is excluded from the first data set by the data processing system 104.

3. Hardware Overview

Figure 4:
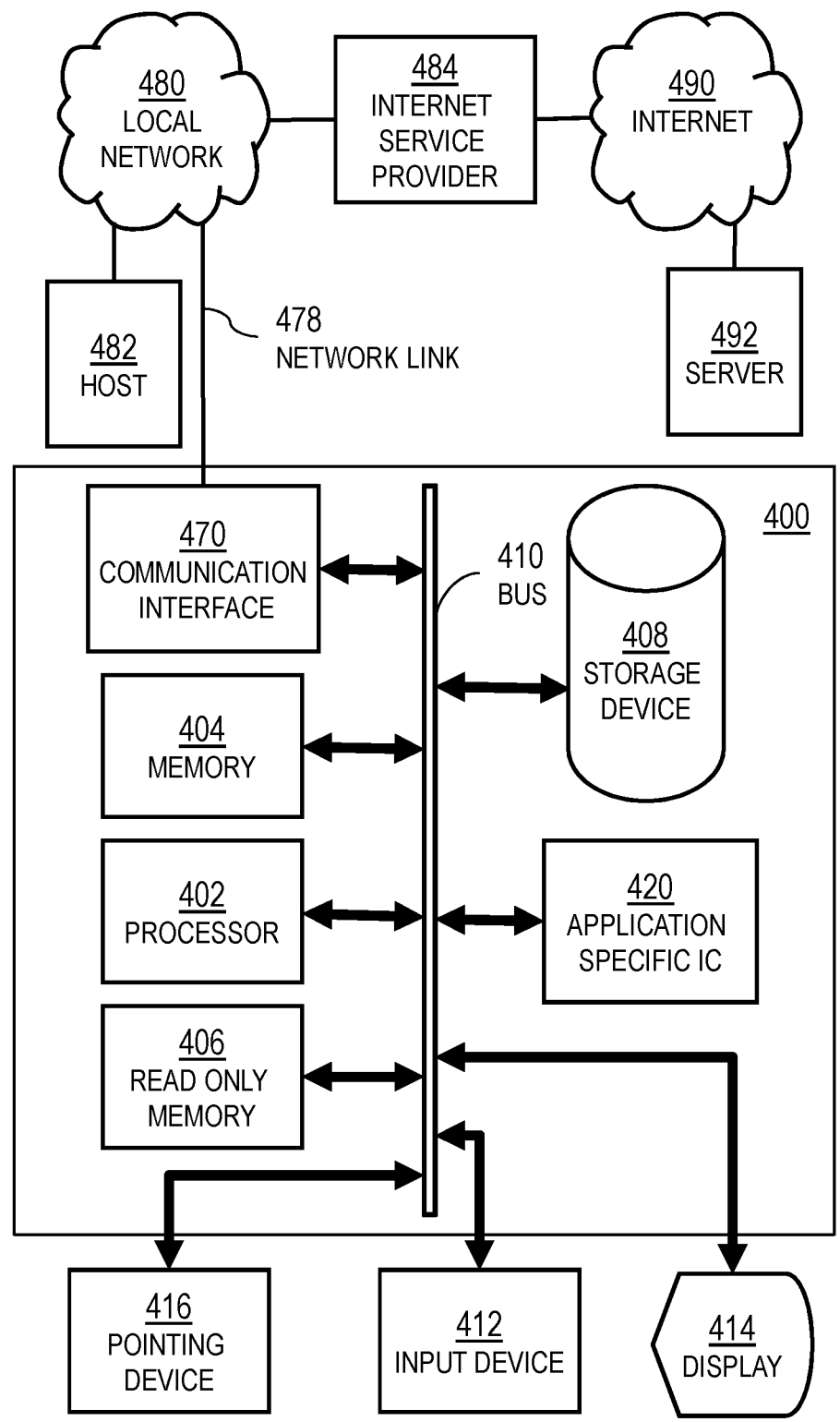
FIG. 4 is a block diagram that illustrates a computer system upon which an embodiment of the invention may be implemented.

FIG. 4 is a block diagram that illustrates a computer system 400 upon which an embodiment of the invention may be implemented. Computer system 400 includes a communication mechanism such as a bus 410 for passing information between other internal and external components of the computer system 400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit)). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 400, or a portion thereof, constitutes a means for performing one or more steps of one or more methods described herein.

A sequence of binary digits constitutes digital data that is used to represent a number or code for a character. A bus 410 includes many parallel conductors of information so that information is transferred quickly among devices coupled to the bus 410. One or more processors 402 for processing information are coupled with the bus 410. A processor 402 performs a set of operations on information. The set of operations include bringing information in from the bus 410 and placing information on the bus 410. The set of operations also typically include comparing two or more units of information, shifting positions of units of information, and combining two or more units of information, such as by addition or multiplication. A sequence of operations to be executed by the processor 402 constitutes computer instructions.

Computer system 400 also includes a memory 404 coupled to bus 410. The memory 404, such as a random access memory (RAM) or other dynamic storage device, stores information including computer instructions. Dynamic memory allows information stored therein to be changed by the computer system 400. RAM allows a unit of information stored at a location called a memory address to be stored and retrieved independently of information at neighboring addresses. The memory 404 is also used by the processor 402 to store temporary values during execution of computer instructions. The computer system 400 also includes a read only memory (ROM) 406 or other static storage device coupled to the bus 410 for storing static information, including instructions, that is not changed by the computer system 400. Also coupled to bus 410 is a non-volatile (persistent) storage device 408, such as a magnetic disk or optical disk, for storing information, including instructions, that persists even when the computer system 400 is turned off or otherwise loses power.

Information, including instructions, is provided to the bus 410 for use by the processor from an external input device 412, such as a keyboard containing alphanumeric keys operated by a human user, or a sensor. A sensor detects conditions in its vicinity and transforms those detections into signals compatible with the signals used to represent information in computer system 400. Other external devices coupled to bus 410, used primarily for interacting with humans, include a display device 414, such as a cathode ray tube (CRT) or a liquid crystal display (LCD), for presenting images, and a pointing device 416, such as a mouse or a trackball or cursor direction keys, for controlling a position of a small cursor image presented on the display 414 and issuing commands associated with graphical elements presented on the display 414.

In the illustrated embodiment, special purpose hardware, such as an application specific integrated circuit (IC) 420, is coupled to bus 410. The special purpose hardware is configured to perform operations not performed by processor 402 quickly enough for special purposes. Examples of application specific ICs include graphics accelerator cards for generating images for display 414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 400 also includes one or more instances of a communications interface 470 coupled to bus 410. Communication interface 470 provides a two-way communication coupling to a variety of external devices that operate with their own processors, such as printers, scanners and external disks. In general the coupling is with a network link 478 that is connected to a local network 480 to which a variety of external devices with their own processors are connected. For example, communication interface 470 may be a parallel port or a serial port or a universal serial bus (USB) port on a personal computer. In some embodiments, communications interface 470 is an integrated services digital network (ISDN) card or a digital subscriber line (DSL) card or a telephone modem that provides an information communication connection to a corresponding type of telephone line. In some embodiments, a communication interface 470 is a cable modem that converts signals on bus 410 into signals for a communication connection over a coaxial cable or into optical signals for a communication connection over a fiber optic cable. As another example, communications interface 470 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 470 sends and receives electrical, acoustic or electromagnetic signals, including infrared and optical signals that carry information streams, such as digital data.

The term computer-readable medium is used herein to refer to any medium that participates in providing information to processor 402, including instructions for execution. Such a medium may take many forms, including, but not limited to, non-volatile media, volatile media and transmission media. Non-volatile media include, for example, optical or magnetic disks, such as storage device 408. Volatile media include, for example, dynamic memory 404. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 402, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 402, except for carrier waves and other signals.

Logic encoded in one or more tangible media includes one or both of processor instructions on a computer-readable storage media and special purpose hardware, such as ASIC 420.

Network link 478 typically provides information communication through one or more networks to other devices that use or process the information. For example, network link 478 may provide a connection through local network 480 to a host computer 482 or to equipment 484 operated by an Internet Service Provider (ISP). ISP equipment 484 in turn provides data communication services through the public, world-wide packet-switching communication network of networks now commonly referred to as the Internet 490. A computer called a server 492 connected to the Internet provides a service in response to information received over the Internet. For example, server 492 provides information representing video data for presentation at display 414.

The invention is related to the use of computer system 400 for implementing the techniques described herein. According to one embodiment of the invention, those techniques are performed by computer system 400 in response to processor 402 executing one or more sequences of one or more instructions contained in memory 404. Such instructions, also called software and program code, may be read into memory 404 from another computer-readable medium such as storage device 408. Execution of the sequences of instructions contained in memory 404 causes processor 402 to perform the method steps described herein. In alternative embodiments, hardware, such as application specific integrated circuit 420, may be used in place of or in combination with software to implement the invention. Thus, embodiments of the invention are not limited to any specific combination of hardware and software.

The signals transmitted over network link 478 and other networks through communications interface 470, carry information to and from computer system 400. Computer system 400 can send and receive information, including program code, through the networks 480, 490 among others, through network link 478 and communications interface 470. In an example using the Internet 490, a server 492 transmits program code for a particular application, requested by a message sent from computer 400, through Internet 490, ISP equipment 484, local network 480 and communications interface 470. The received code may be executed by processor 402 as it is received, or may be stored in storage device 408 or other non-volatile storage for later execution, or both. In this manner, computer system 400 may obtain application program code in the form of a signal on a carrier wave.

Various forms of computer readable media may be involved in carrying one or more sequence of instructions or data or both to processor 402 for execution. For example, instructions and data may initially be carried on a magnetic disk of a remote computer such as host 482. The remote computer loads the instructions and data into its dynamic memory and sends the instructions and data over a telephone line using a modem. A modem local to the computer system 400 receives the instructions and data on a telephone line and uses an infra-red transmitter to convert the instructions and data to a signal on an infra-red a carrier wave serving as the network link 478. An infrared detector serving as communications interface 470 receives the instructions and data carried in the infrared signal and places information representing the instructions and data onto bus 410. Bus 410 carries the information to memory 404 from which processor 402 retrieves and executes the instructions using some of the data sent with the instructions. The instructions and data received in memory 404 may optionally be stored on storage device 408, either before or after execution by the processor 402.

Figure 5:
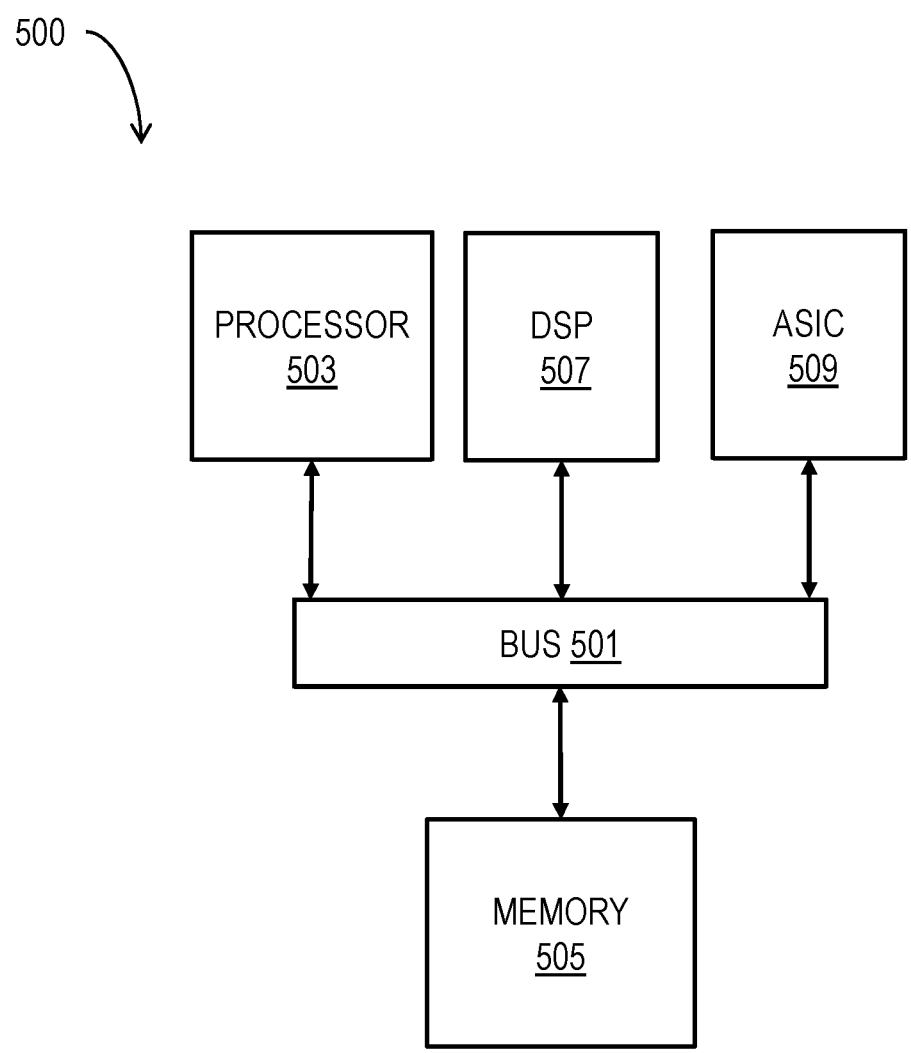
FIG. 5 is a block diagram that illustrates a chip set upon which an embodiment of the invention may be implemented.

FIG. 5 illustrates a chip set 500 upon which an embodiment of the invention may be implemented. Chip set 500 is programmed to perform one or more steps of a method described herein and includes, for instance, the processor and memory components described with respect to FIG. 4 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 500, or a portion thereof, constitutes a means for performing one or more steps of a method described herein.

In one embodiment, the chip set 500 includes a communication mechanism such as a bus 501 for passing information among the components of the chip set 500. A processor 503 has connectivity to the bus 501 to execute instructions and process information stored in, for example, a memory 505. The processor 503 may include one or more processing cores with each core configured to perform independently. A multi-core processor enables multiprocessing within a single physical package. Examples of a multi-core processor include two, four, eight, or greater numbers of processing cores. Alternatively or in addition, the processor 503 may include one or more microprocessors configured in tandem via the bus 501 to enable independent execution of instructions, pipelining, and multithreading. The processor 503 may also be accompanied with one or more specialized components to perform certain processing functions and tasks such as one or more digital signal processors (DSP) 507, or one or more application-specific integrated circuits (ASIC) 509. A DSP 507 typically is configured to process real-world signals (e.g., sound) in real time independently of the processor 503. Similarly, an ASIC 509 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 503 and accompanying components have connectivity to the memory 505 via the bus 501. The memory 505 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 505 also stores the data associated with or generated by the execution of one or more steps of the methods described herein.

4. Extensions, Modifications and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method comprising:
    obtaining, on a processor, first data that indicates values for one or more parameters of a characteristic of a continuous photoplethysmographic (PPG) waveform collected by a pulse oximeter during a fixed time interval of a treatment of a patient, wherein the characteristic of the PPG waveform includes one or more of a heart rate and an oxygen saturation and wherein the one or more parameters include one or more of:
        a percentage of the fixed time interval that the heart rate is below a threshold heart rate,
        a percentage of the fixed time interval that the oxygen saturation is below a threshold saturation rate,
        a percentile of the oxygen saturation over the fixed time interval,
        a percentile of an amplitude of the PPG waveform over the fixed time interval,
        an area of a heart rate waveform of the PPG waveform below a low threshold heart rate or above a high threshold heart rate over the fixed time interval, and
        an area of an oxygen saturation waveform of the PPG waveform below a threshold saturation rate,
    applying, on the processor, coefficients to the values for the one or more parameters;
    determining, on the processor, second data that indicates a prediction that the patient will require a blood transfusion during a time range within a time period of at least 15 minutes after the fixed time interval of the treatment based on applying the coefficients to the values for the one or more parameters, wherein the prediction is based on the time range;
    presenting, on a display device, output data based on the second data wherein the output data indicates one or more units of blood to be ordered; and
    ordering the one or more units of blood for the patient based on the output data.

2. The method of claim 1, wherein the low threshold heart rate is 60 beats per minute, the threshold saturation rate is 95%, the percentile of the oxygen saturation comprises a first percentile that is 25 percentile and a second percentile that is 50 percentile.

3. The method of claim 1, wherein the prediction is based on the time range of up to 3 hours after the collection of the first data, wherein the low threshold heart rate is 60 beats per minute, the threshold saturation rate is 95%, the percentile of the oxygen saturation comprises a first percentile that is 25 percentile and a second percentile that is 50 percentile;
    and wherein the coefficient for the percentage of the fixed time interval that the heart rate is below the low threshold heart rate is in a range from 0.84 to 4.93, the coefficient for the percentage of the fixed time interval that the oxygen saturation is below the threshold saturation rate is in a range from 0.05 to 3.45, the coefficient for the first percentile is in a range from 0.33 to 2.68 and the coefficient for the second percentile is in a range from 0.04 to 2.11.

4. The method of claim 1, wherein the prediction is based on the time range of up to 6 hours after the collection of the first data, wherein the low threshold heart rate is 60 beats per minute, the threshold saturation rate is 86%, the percentile of the oxygen saturation comprises a first percentile that is 25 percentile and a second percentile that is 50 percentile;
    and wherein the coefficient for the percentage of the fixed time interval that the heart rate is below the low threshold heart rate is in a range from 0.85 to 5.18, the coefficient for the percentage of the fixed time interval that the oxygen saturation is below the threshold saturation rate is in a range from 2.45 to 9.45, the coefficient for the first percentile is in a range from 0.41 to 2.93 and the coefficient for the second percentile is in a range from 0.01 to 2.20.

5. The method of claim 1, wherein the prediction is based on the time range of up to 12 hours after the collection of the first data, wherein the low threshold heart rate is 60 beats per minute, the threshold saturation rate is 95%, the percentile of the oxygen saturation comprises a first percentile that is 25 percentile and a second percentile that is 50 percentile;
    and wherein the coefficient for the percentage of the fixed time interval that the heart rate is below the low threshold heart rate is in a range from 0.41 to 2.80, the coefficient for the percentage of the fixed time interval that the oxygen saturation is below the threshold saturation rate is in a range from 0.04 to 0.26, the coefficient for the first percentile is in a range from −0.11 to 1.72 and the coefficient for the second percentile is in a range from −0.05 to 1.81.

6. The method of claim 1, wherein the prediction is based on the time range of up to 24 hours after the collection of the first data, wherein the low threshold heart rate is 60 beats per minute and the threshold saturation rate is 95%;
    and wherein the coefficient for the percentage of the fixed time interval that the heart rate is below the low threshold heart rate is in a range from 1.11 to 3.31 and the coefficient for the percentage of the fixed time interval that the oxygen saturation is below the threshold saturation rate is in a range from 0.41 to 3.82.

7. The method of claim 1, wherein the parameter is the percentile of the amplitude of the PPG waveform collected over the fixed time interval.

8. The method of claim 7, wherein the parameter is one or more of a 10 percentile, 20 percentile, 25 percentile, 30 percentile, 40 percentile, 50 percentile, 60 percentile, 70 percentile, 75 percentile, 80 percentile, and 90 percentile of the amplitude of the PPG waveform collected over the fixed time interval.

9. The method of claim 1, wherein the parameter includes one or more of the area of the heart rate waveform below the low threshold heart rate or above the high threshold heart rate and the area of the oxygen saturation waveform below the threshold oxygen saturation rate.

10. The method of claim 9, wherein the low threshold heart rate is one of 60 beats per minute or 72 beats per minute, the high threshold heart rate is one of 100 beats per minute, 110 beats per minute and 120 beats per minute, and the threshold oxygen saturation rate is one or more of 98%, 95%, 92%, 90% and 86%.

11. The method of claim 1 further comprising obtaining, on the processor, third data that indicates values for one or more secondary parameters of a characteristic of the patient;
    wherein applying the coefficients to the one or more parameters further includes applying coefficients to the values for the one or more secondary parameters;

and wherein the secondary parameters include one or more of an age and a gender of the patient.

12. The method of claim 1, further comprising determining, on the processor, values for the coefficients of the one or more parameters including:
obtaining, on the processor, preliminary data for the one or more parameters of the characteristic of the PPG waveform during treatment of a plurality of patients;
assigning, on the processor, a result for each patient based on whether the patient received a blood transfusion during the treatment;
fitting, on the processor, the preliminary data to the results for the plurality of patients; and
determining, on the processor, the coefficients for the one or more parameters, to determine a model for predicting whether a patient will require a blood transfusion based on the first data.

13. The method of claim 1, further comprising:
applying, on the processor, secondary coefficients to the values of the one or more parameters; and
determining, on the processor, fourth data that indicates a prediction that the patient will require a massive blood transfusion of at least five blood units during the treatment based on applying the secondary coefficients to the values for the one or more parameters.

14. A method comprising:
obtaining, on a processor, data that indicates values for one or more parameters of a characteristic of a continuous photoplethysmographic (PPG) waveform collected by a pulse oximeter during a fixed time interval of a treatment of a plurality of patients, wherein the characteristic of the PPG waveform includes one or more of a heart rate and an oxygen saturation and wherein the one or more parameters include one or more of:
a percentage of the fixed time interval that the heart rate is below a threshold heart rate,
a percentage of the fixed time interval that the oxygen saturation is below a threshold saturation rate,
a percentile of the oxygen saturation over the fixed time interval,
a percentile of an amplitude of the PPG waveform over the fixed time interval,
an area of a heart rate waveform of the PPG waveform below a low threshold heart rate or above a high threshold heart rate over the fixed time interval, and
an area of an oxygen saturation waveform of the PPG waveform below a threshold saturation rate,
assigning, on the processor, a result for each patient based on whether the patient received a blood transfusion during a time range within a time period of at least 15 minutes after the fixed time interval of the treatment;
fitting, on the processor, the data to the results for the plurality of patients;
determining, on the processor, coefficients for the one or more parameters, to determine a model for predicting whether a patient will require a blood transfusion during the time range based on an input of the one or more parameters;
presenting, on a display device, output data based on the model for predicting whether the patient will require the blood transfusion and the input of the one or more parameters, wherein the output data indicates one or more units of blood to be ordered; and
ordering the one or more units of blood for the patient based on the output data.

15. The method of claim 14,
wherein a result is assigned to each patient during a plurality of time ranges of the treatment based on whether each patient received a blood transfusion during each of the plurality of time ranges;
wherein the data is fit to each respective result for the plurality of patients during the plurality of time ranges;
wherein the coefficients for the one or more parameters are obtained for each of the plurality of time ranges, to determine a model for predicting whether a patient will require a blood transfusion during each of the plurality of time ranges based on an input of the one or more parameters.

16. An apparatus comprising:
a pulse oximeter configured to measure first data that indicates values for one or more parameters of a characteristic of a continuous photoplethysmographic (PPG) waveform collected during a fixed time interval of a treatment of a patient, wherein the characteristic of the PPG waveform includes one or more of a heart rate and an oxygen saturation and wherein the one or more parameters include one or more of:
a percentage of the fixed time interval that the heart rate is below a threshold heart rate,
a percentage of the fixed time interval that the oxygen saturation is below a threshold saturation rate,
a percentile of the oxygen saturation over the fixed time interval,
a percentile of an amplitude of the PPG waveform over the fixed time interval,
an area of a heart rate waveform of the PPG waveform below a low threshold heart rate or above a high threshold heart rate over the fixed time interval, and
an area of an oxygen saturation waveform of the PPG waveform below a threshold saturation rate,
at least one processor connected to the pulse oximeter to receive the first data of the one or more parameters; and
at least one memory including one or more sequence of instructions;
the at least one memory and the one or more sequence of instructions configured to, with the at least one processor, cause the apparatus to perform at least the following:
apply coefficients to the values for the one or more parameters, and
determine second data that indicates a prediction that the patient will require a blood transfusion during a time range within a time period of at least 15 minutes after the fixed time interval of the treatment based on applying the coefficients to the values for the one or more parameters, wherein the prediction is based on the time range,
present on a display device output data based on the second data wherein the output data indicates one or more units of blood to be ordered, and
order the one or more units of blood for the patient based on the output data.

17. The apparatus of claim 16, wherein the prediction is based on the time range of up to 3 hours after the collection of the first data, wherein the low threshold heart rate is 60 beats per minute, the threshold saturation rate is 95%, the percentile of the oxygen saturation comprises a first percentile that is 25 percentile and a second percentile that is 50 percentile;
and wherein the coefficient for the percentage of the fixed time interval that the heart rate is below the low threshold heart rate is in a range from 0.84 to 4.93, the coefficient for the percentage of the fixed time interval that the oxygen saturation is below the threshold saturation rate is in a range from 0.05 to 3.45, the coefficient for the first percentile is in a range from 0.33 to 2.68 and the coefficient for the second percentile is in a range from 0.04 to 2.11.

18. The apparatus of claim 16, wherein the prediction is based on the time range of up to 6 hours after the collection of the first data, wherein the low threshold heart rate is 60 beats per minute, the threshold saturation rate is 86%, the percentile of the oxygen saturation comprises a first percentile that is 25 percentile and a second percentile that is 50 percentile;

and wherein the coefficient for the percentage of the fixed time interval that the heart rate is below the low threshold heart rate is in a range from 0.85 to 5.18, the coefficient for the percentage of the fixed time interval that the oxygen saturation is below the threshold saturation rate is in a range from 2.45 to 9.45, the coefficient for the first percentile is in a range from 0.41 to 2.93 and the coefficient for the second percentile is in a range from 0.01 to 2.20.

19. The apparatus of claim 16, wherein the prediction is based on the time range of up to 12 hours after the collection of the first data, wherein the low threshold heart rate is 60 beats per minute, the threshold saturation rate is 95%, the percentile of the oxygen saturation comprises a first percentile that is 25 percentile and a second percentile that is 50 percentile;

and wherein the coefficient for the percentage of the fixed time interval that the heart rate is below the low threshold heart rate is in a range from 0.41 to 2.80, the coefficient for the percentage of the fixed time interval that the oxygen saturation is below the threshold saturation rate is in a range from 0.04 to 0.26, the coefficient for the first percentile is in a range from −0.11 to 1.72 and the coefficient for the second percentile is in a range from −0.05 to 1.81.

20. A non-transitory computer-readable medium carrying one or more sequences of instructions, wherein execution of the one or more sequences of instructions by one or more processors causes the one or more processors to perform the steps of:

applying coefficients to values for one or more parameters of a characteristic of a continuous photoplethysmographic (PPG) waveform collected by a pulse oximeter during a fixed interval of a treatment of a patient, wherein the characteristic of the PPG waveform includes one or more of a heart rate and an oxygen saturation and wherein the one or more parameters include one or more of:

a percentage of the fixed time interval that the heart rate is below a threshold heart rate, a percentage of the fixed time interval that the oxygen saturation is below a threshold saturation rate, a percentile of the oxygen saturation over the fixed time interval, a percentile of an amplitude of the PPG waveform over the fixed time interval, an area of a heart rate waveform of the PPG waveform below a low threshold heart rate or above a high threshold heart rate over the fixed time interval, and an area of an oxygen saturation waveform of the PPG waveform below a threshold saturation rate;

determining a prediction that the patient will require a blood transfusion during a time range within a time period of at least 15 minutes after the fixed interval of the treatment based on applying the coefficients to the values for the one or more parameters, wherein the prediction is based on the time range;

presenting on a display device output data based on the prediction, wherein the output data indicates one or more units of blood to be ordered; and ordering the one or more units of blood for the patient based on the prediction.

\* \* \* \* \*